United States Patent
Patel et al.

(10) Patent No.: US 9,909,193 B2
(45) Date of Patent: Mar. 6, 2018

(54) DIAGNOSTIC METHODS AND COMPOSITIONS

(71) Applicant: Theranos, Inc., Palo Alto, CA (US)

(72) Inventors: Pranav Patel, Palo Alto, CA (US); Indira Wu, Palo Alto, CA (US); Aaron Richardson, Palo Alto, CA (US); Kamila Belhocine, Palo Alto, CA (US); Josephine Lee, Palo Alto, CA (US); Scott Tabakman, Palo Alto, CA (US)

(73) Assignee: Theranos IP Company, LLC, Newark, CA (US)

( * ) Notice: Subject to any disclaimer, the term of this patent is extended or adjusted under 35 U.S.C. 154(b) by 0 days.

(21) Appl. No.: 15/087,840

(22) Filed: Mar. 31, 2016

(65) Prior Publication Data

US 2016/0201148 A1    Jul. 14, 2016

Related U.S. Application Data

(63) Continuation of application No. PCT/US2015/050811, filed on Sep. 17, 2015, which is a continuation-in-part of application No. PCT/US2014/056151, filed on Sep. 17, 2014.

(60) Provisional application No. 62/051,912, filed on Sep. 17, 2014, provisional application No. 62/051,945, filed on Sep. 17, 2014, provisional application No. 62/068,603, filed on Oct. 24, 2014, provisional application No. 62/068,605, filed on Oct. 24, 2014, provisional application No. 62/151,358, filed on Apr. 22, 2015.

(51) Int. Cl.
*C12Q 1/68* (2006.01)
*C12Q 1/70* (2006.01)

(52) U.S. Cl.
CPC ......... *C12Q 1/707* (2013.01); *C12Q 1/6858* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,498,131 B2 * | 3/2009 | Van Eijk | C12Q 1/6827 435/6.12 |
| 2002/0081598 A1 | 6/2002 | Evans et al. | |
| 2008/0153763 A1 | 6/2008 | Takagi et al. | |
| 2012/0070831 A1 | 3/2012 | Johnson | |

FOREIGN PATENT DOCUMENTS

| | | |
|---|---|---|
| JP | 2005137287 A | 6/2005 |
| JP | 2014140367 | 8/2014 |
| WO | 2014145296 A2 | 9/2014 |

(Continued)

OTHER PUBLICATIONS

International Search Report and Written Opinion dated Feb. 9, 2016 for PCT/US2015/050811.

(Continued)

*Primary Examiner* — Stephanie K Mummert

(57) ABSTRACT

Methods and compositions for the identification of genetic-related information are provided. At least portions of methods provided herein may be performed without thermocycling. Methods and compositions may include reagents such as nucleic acid polymerases and primers.

10 Claims, 5 Drawing Sheets

(56) References Cited

FOREIGN PATENT DOCUMENTS

| WO | WO2014145296 | * | 9/2014 | ............... | C12Q 1/68 |
|----|--------------|---|--------|-----------------|-----------|
| WO | 2015076919 A1 | | 5/2015 | | |
| WO | 2016044664 A1 | | 3/2016 | | |

OTHER PUBLICATIONS

Kimura et al. Optimization of turn-back primers in isothermal amplification. Nucleic Acids Res., 2011, 39(9), e59.

* cited by examiner

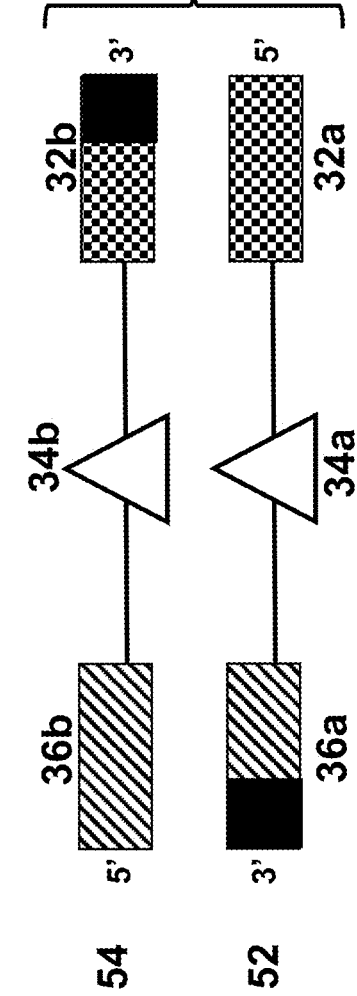
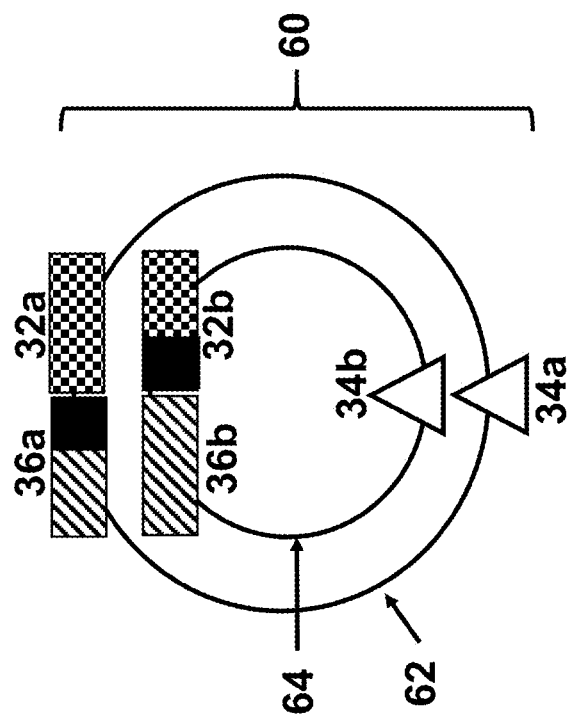

SEQUENCE LISTING

```
<160> NUMBER OF SEQ ID NOS: 20

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggaacgagga ccatcgcatc acccaagggt cctgttatcc agatgtatac caatgtagac     60

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```
cgcaggtgca gggtgtcaat gagcgggcac cttgaggagc gggccagccc acgaggtct        59

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaaccaacgc atgacccaag                                                   20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttgaaccaac gcatgaccc                                                    19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagacgaaaa agcaccagaa                                                   20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaccagaaa atatgagcga c                                                 21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atccggtact gcagaactca                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gcaaatccgg tactgcagaa                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attggcaaat ccggtactgc                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcagacaaa ttgggtggtt                                                  20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gccaatgacg aatacaaagt c                                                21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taatagccat catcatgttt gg                                               22

<210> SEQ ID NO 13
<211> LENGTH: 121
<212> TYPE: DNA
<213> ORGANISM: Hepatitis C virus

<400> SEQUENCE: 13
ggaacgagga ccatcgcatc acccaagggt cctgttatcc agatgtatac caatgtagac      60
caagacctcg tgggctggcc cgctcctcaa ggtgcccgct cattgacacc ctgcacctgc     120
g                                                                    121

<210> SEQ ID NO 14
<211> LENGTH: 121
<212> TYPE: DNA
<213> ORGANISM: Hepatitis C virus

<400> SEQUENCE: 14
ggaacgagga ccatcgcatc acccaagggt cctgttatcc agatgtatac caatgtagac      60
aaagacctcg tgggctggcc cgctcctcaa ggtgcccgct cattgacacc ctgcacctgc     120
``` g                                                                              121

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttgtctaaa gggtcctgtt atcc                                                      24

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tagacaaaca gcccacgagg                                                           20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttgtctagt tatccagatg tat                                                       23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tagacaaacc agcccacgag gtc                                                       23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcttggtcca agggtcctgt tatc                                                      24

<210> SEQ ID NO 20
<211> LENGTH: 23
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 20
gaccaagaag ggtgtcaatg agc                                              23
```

DIAGNOSTIC METHODS AND COMPOSITIONS

RELATED APPLICATIONS

This application is a continuation of International Application No. PCT/US2015/050811, filed Sep. 17, 2015, which claims priority to International Application No. PCT/US2014/056151, filed Sep. 17, 2014, U.S. Provisional Application No. 62/051,912, filed Sep. 17, 2014, U.S. Provisional Application No. 62/051,945, filed Sep. 17, 2014, U.S. Provisional Application No. 62/068,603, filed Oct. 24, 2014, U.S. Provisional Application No. 62/068,605, filed Oct. 24, 2014, and U.S. Provisional Application No. 62/151,358, filed Apr. 22, 2015, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 25, 2016, is named 3034.501_SL.txt and is 5,143 bytes in size.

BACKGROUND

In order effectively diagnose or treat a subject suffering from a mutation in the subject's gene or from an infection with a pathogen, it is frequently desirable to obtain detailed genetic information relating to the mutation or the pathogen.

For example, methicillin-resistant *Staphylococcus aureus* (MRSA) is a type of *Staphylococcus aureus* (*S. aureus*) which can cause infection in humans and is resistant to beta-lactam antibiotics. As a result of its resistance to certain antibiotics, MRSA infections can be difficult to treat.

*S. aureus* bacteria typically become methicillin-resistant through acquiring the mecA gene. The mecA gene is typically located in the staphyloccal cassette chromosome mec (SCCmec), which is a multi-gene, transferable genomic element. Different types of SCCmec exist, with known SCCmec types ranging in size from approximately 21,000-67,000 nucleotides in length. Generally, within each type of SCCmec, the mecA gene is surrounded by other genes or elements which are other components of the SCCmec. In MRSA bacteria, SCCmec containing the mecA gene is integrated into the *S. aureus* chromosome.

In order identify and control MRSA bacteria, effective reagents and methods for MRSA detection are needed. In addition, improved reagents and methods for assessing other integrated genes in host genetic material and also for assessing whether two or more genetic elements are in a common molecule are needed.

As another example, within Hepatitis C genotype 1a, there is a polymorphic site Q80K in the protease gene, nonstructural protein 3 ("NS3"; also known as "p-70"), that is associated with treatment failure with the protease inhibitor boceprevir, which otherwise can be effective in blocking peptide maturation in the virus. Assessing the Q80 polymorphism in the NS3 gene in patients with subtype 1a can be an important part of formulating a treatment plan.

Accordingly, improved reagents and methods for assessing the Q80 polymorphism are needed. In addition, improved reagents and methods for assessing other SNPs, point mutations, and other nucleotide variations are needed.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, in the event of a conflict between the content of the present express disclosure and the content of a document incorporated by reference herein, the content of the present express disclosure controls.

SUMMARY

Provided herein are methods and compositions relating to the identification of genetic-related information. In embodiments, improved reagents and methods for assessing integrated genes in host genetic material are provided. For example, improved reagents and methods for MRSA detection are provided. In embodiments, improved reagents and methods for assessing whether at least a first genetic element and a second genetic element are both on a common nucleic acid molecule are provided. In such embodiments, the first genetic element and the second genetic element may be separated from each other on the common nucleic acid molecule by a large number of nucleotides. In other embodiments, improved reagents and methods for assessing SNPs and point mutations are provided. For example, improved reagents and methods for assessing the Q80 polymorphism in the Hepatitis C NS3 gene are provided.

In embodiments, provided herein is a method for detecting a first genetic element and a second genetic element on a common double-stranded nucleic acid molecule, the method comprising: performing a first amplification reaction in a first amplification reaction mixture, wherein the first amplification reaction mixture comprises: i) the common double-stranded nucleic acid molecule, wherein the common double-stranded nucleic acid molecule comprises a first strand and a second strand, and also the first genetic element and the second genetic element, wherein the first genetic element comprises a first genetic element first complementary sequence and a first genetic element second complementary sequence, wherein the second genetic element comprises a second genetic element first complementary sequence and a second genetic element second complementary sequence, wherein the first genetic element first complementary sequence and the second genetic element first complementary sequence are part of the first strand, and wherein the first genetic element second complementary sequence and the second genetic element second complementary sequence are part of the second strand; ii) a first amplification reaction first primer, wherein the first amplification reaction first primer has a nucleotide sequence which is complementary to the first genetic element first complementary sequence; and iii) a first amplification reaction second primer, wherein the first amplification reaction second primer has a nucleotide sequence which is complementary to the second genetic element second complementary sequence, and wherein a first amplification reaction product is generated in the first amplification reaction mixture, wherein the first amplification reaction product comprises at least a portion of the first genetic element and at least a portion of the second genetic element, and wherein the first amplification reaction product has a double-stranded, linear configuration; performing a ligation reaction in a ligation reaction mixture, wherein the ligation reaction mixture comprises i) the first amplification reaction product; and ii) a ligase enzyme, and wherein in the ligation reaction mixture a circular ligation product is formed from the first amplification reaction product, wherein the circular ligation product is double-stranded and comprises a circular ligation product first strand and a circular ligation product second strand, and wherein the circular ligation product first strand comprises the nucleotides of the first amplification reaction product first strand and the circular ligation product second strand comprises the nucleotides of the first amplification reaction product second strand; and performing a second amplification reaction in a second amplification reaction mixture, wherein the second amplification reaction mixture comprises: i) the circular ligation product; ii) a second amplification reaction first primer, wherein the second amplification reaction first primer has a nucleotide sequence which is complementary to the first genetic element second complementary sequence; and iii) a second amplification reaction second primer, wherein the second amplification reaction second primer has a nucleotide sequence which is complementary to the second genetic element first complementary sequence, and wherein a second amplification reaction product is generated in the second amplification reaction mixture, wherein the second amplification reaction product comprises at least a portion of the first genetic element and at least a portion of the second genetic element; and detecting the second amplification reaction product. Optionally, the method may further comprise, prior to performing the ligation reaction, incubating the first amplification reaction product with a kinase enzyme.

In embodiments, in a composition or method provided herein involving a double-stranded nucleic acid molecule comprising a first genetic element and a second genetic element, the first genetic element and the second genetic element may be separated from each other on the double-stranded nucleic acid molecule by at least 100, 200, 500, 1000, 2000, 3000, 4000, 5000, 10,000, 15,000, 20,000, 25,000, or 30,000 and no more than 200, 500, 1000, 2000, 3000, 4000, 5000, 10,000, 15,000, 20,000, 25,000, 30,000, 40,000, 50,000, 60,000, 70,000, 80,000, 90,000, or 100,000 nucleotides.

In embodiments, in a method or composition provided herein involving a first amplification reaction, the first amplification reaction may be a PCR amplification reaction or a non-thermocycling amplification reaction.

In embodiments, in a method or composition provided herein involving a second amplification reaction, the second amplification reaction may be a PCR amplification reaction or a non-thermocycling amplification reaction.

In embodiments, in a method or composition provided herein involving a first primer and a second primer, the first primer and the second primer are each at least 4, 5, 6, 7, 8, 9, 10, 11, 12, 15, 20, or 25 and no more than 5, 6, 7, 8, 9, 10, 11, 12, 15, 20, 25, 30, 40, 50, 60, 70, 80, 90, or 100 nucleotides in length.

In embodiments, in a method or composition provided herein involving a first primer and a second primer, at least one or both of the first primer and the second primer in the first amplification reaction mixture is phosphorylated at the 5' end of the primer.

In embodiments, in a method or composition provided herein involving a kinase enzyme, the kinase enzyme is T4 polynucleotide kinase.

In embodiments, in a method or composition provided herein involving a ligase enzyme, the ligase enzyme is T4 DNA ligase.

In embodiments, in a method or composition provided herein involving a second amplification reaction first primer and a second amplification reaction second primer.

In embodiments, in a method or composition provided herein involving a second amplification reaction first primer and a second amplification reaction second primer, the second amplification reaction first primer comprises a first region and a second region, wherein the second region of the second amplification reaction first primer is complementary to the second genetic element first complementary sequence and the second amplification reaction second primer comprises a first region and a second region, wherein the second region of the second amplification reaction second primer is complementary to the first genetic element second complementary sequence, and wherein the first region of the second amplification reaction second primer is complementary to the first region of the second amplification reaction first primer. Optionally, the first region of the second amplification reaction second primer is also complementary to at least a portion of the first strand of the circular ligation product.

In embodiments, in a method or composition provided herein involving a second amplification reaction product, the second amplification reaction product is detected in real-time as it is generated.

In embodiment, in a method or composition provided herein involving a first genetic element, the first genetic element is an antibiotic resistance gene, such as the mecA gene.

In embodiment, in a method or composition provided herein involving a second genetic element, the second genetic element is a pathogen gene, such as from *Staphylococcus aureus*.

In embodiments, a method provided herein may further comprise obtaining a biological sample from a subject, wherein the biological sample from the subject contains a common double-stranded nucleic acid molecule or a polynucleotide template. In embodiments, the biological sample may be obtained from a subject's digit. In embodiments, the biological sample may have a volume of no greater than 500, 400, 300, 200, 100, or 50 microliters.

In embodiments, in a method or composition provided herein involving a biological sample from a subject which contains a common double-stranded nucleic acid molecule, the sample contains the common double-stranded nucleic acid molecule in a methicillin-resistant *Staphylococcus aureus* organism.

In embodiments, in a method or composition provided herein involving a first amplification reaction, a ligation reaction, and a second amplification reaction, the first amplification reaction, the ligation reaction, and the second amplification reaction all occur in the same vessel.

In embodiments, in a method or composition provided herein involving a first amplification reaction, a ligation reaction, and a second amplification reaction, the first amplification reaction, the ligation reaction, and the second amplification reaction occur in different vessels.

In embodiments, in a method or composition provided herein involving a ligation reaction, the ligation reaction may result in one or both of a circular ligation product or an end-to-end ligation product.

In embodiments, provided herein is a method for assessing the identity of a nucleotide at a position of interest in a nucleotide sequence in a polynucleotide template, the method comprising: A) generating multiple copies of a polynucleotide template in a polymerase chain reaction (PCR) amplification reaction mixture, wherein the PCR amplification reaction mixture comprises a PCR amplification reaction first primer and a PCR amplification reaction second primer, wherein in the PCR amplification reaction mixture, the PCR amplification reaction first primer anneals to the polynucleotide template and the PCR second primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template; B) providing copies of the PCR amplification reaction product generated in step A) in each of at least a non-thermocycling first reaction mixture and a non-thermocycling second reaction mixture, wherein: the polynucleotide template comprises a first portion, a second portion and a third portion, wherein the third portion is situated in the polynucleotide template between the first portion and the second portion and wherein the position of interest is in the third portion; the non-thermocycling first reaction mixture comprises copies of the polynucleotide template, a non-thermocycling first primer, and a non-thermocycling second primer, wherein: the non-thermocycling first primer comprises a first region and a second region, wherein the first region comprises a 5' end of the primer, the second region comprises a 3' end of the primer, and the second region is complementary to the first portion of the polynucleotide template; the non-thermocycling second primer comprises a first region and a second region, wherein the first region comprises a 5' end of the primer, the second region comprises a 3' end of the primer, and the second region is complementary to a sequence which is complementary to a second portion of the polynucleotide template; the first region of the non-thermocycling first primer is complementary to the first region of the non-thermocycling second primer; and the first region of the non-thermocycling second primer is complementary to the third portion of the polynucleotide template; the second reaction mixture comprises copies of the polynucleotide template, a non-thermocycling third primer, and a non-thermocycling fourth primer, wherein: the non-thermocycling third primer comprises a first region and a second region, wherein the first region comprises a 5' end of the primer, the second region comprises a 3' end of the primer, and the second region is complementary to the first portion of the polynucleotide template; the non-thermocycling fourth primer comprises a first region and a second region, wherein the first region comprises a 5' end of the primer, the second region comprises a 3' end of the primer, and the second region is complementary to a sequence which is complementary to a second portion of the polynucleotide template; the first region of the non-thermocycling third primer is complementary to the first region of the non-thermocycling fourth primer; and the first region of the non-thermocycling fourth primer is complementary to the third portion of the polynucleotide template; and the nucleotide sequence of the first region of the non-thermocycling second primer differs from the nucleotide sequence of first region of the non-thermocycling fourth primer by a single nucleotide, wherein the position of the different nucleotide in the non-thermocycling second and non-thermocycling fourth primers corresponds to the position of the nucleotide of interest in the polynucleotide template when the nucleotide sequence of the first region of the non-thermocycling second primer or non-thermocycling fourth primer is oriented with the nucleotide sequence of the third portion of the polynucleotide template for maximum complementation of the sequences; C) incubating the non-thermocycling first reaction mixture and non-thermocycling second reaction mixture under conditions without thermocycling; and D) comparing the rate or amount of amplification of the polynucleotide template in the non-thermocycling first reaction mixture to the rate or amount of amplification of the polynucleotide template in the non-thermocycling second reaction mixture, wherein the rate or amount of amplification of the polynucleotide template is indicative of the degree of complementation between first region of the non-thermocycling second or non-thermocycling fourth primer and the nucleotide sequence of the third portion of the polynucleotide template. Optionally, the PCR amplification reaction first primer is at least 5, 6, 7, 8, 9, 10, 11, 12, 13, 14, 15, 20, 25, 30, 40, 50, or 60 and no more than 10, 11, 12, 13, 14, 15, 20, 25, 30, 40, 50, 60, 70, 80, 90, or 100 nucleotides in length, and wherein when the PCR amplification reaction first primer is annealed to the polynucleotide template, at least 1, 2, 3, 4, 5, 6, 7, 8, 9, or 10 nucleotides of the PCR amplification reaction first primer are mis-matched according to Watson-Crick base-pairing rules with corresponding nucleotides on the polynucleotide template. Optionally, the PCR amplification reaction second primer is at least 5, 6, 7, 8, 9, 10, 11, 12, 13, 14, 15, 20, 25, 30, 40, 50, or 60 and no more than 10, 11, 12, 13, 14, 15, 20, 25, 30, 40, 50, 60, 70, 80, 90, or 100 nucleotides in length, and wherein when the PCR amplification reaction second primer is annealed to the polynucleotide which is complementary to the polynucleotide template, at least 1, 2, 3, 4, 5, 6, 7, 8, 9, or 10 nucleotides of the PCR amplification reaction second primer are mis-matched according to Watson-Crick base-pairing rules with corresponding nucleotides on the polynucleotide which is complementary to the polynucleotide template.

In embodiments, in a method or composition provided herein involving a position of interest in a nucleotide sequence in a polynucleotide template, the position of interest in the nucleotide sequence in the polynucleotide template is a SNP.

In embodiments, a polynucleotide template provided herein may be from the hepatitis C virus, optionally specifically from the hepatitis C NS3 gene. In embodiments, in a method or composition provided herein involving a position of interest in a nucleotide sequence in a polynucleotide template, the position of interest in the nucleotide sequence in the polynucleotide template is in the codon encoding $80^{th}$ amino acid of the NS3 gene of hepatitis C.

In embodiments, provided herein is a method for amplifying a polynucleotide template, the method comprising: A) generating multiple copies of a polynucleotide template in a polymerase chain reaction (PCR) amplification reaction mixture, wherein the PCR amplification reaction mixture comprises a first PCR amplification reaction primer and a second PCR amplification reaction primer, wherein in the PCR amplification reaction mixture, the first PCR amplification reaction primer anneals to the polynucleotide template and the second PCR amplification reaction primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template; B) incubating copies of the polynucleotide template in a non-thermocycling reaction mixture comprising a non-thermocycling reaction first primer and a non-thermocycling reaction second primer, wherein: the polynucleotide template comprises a first portion, a second portion and a third portion, wherein the third portion is situated in the polynucleotide template between the first portion and the second portion; the first primer comprises a first region and a second region, wherein the second region of the first primer is complementary to the first portion of the polynucleotide template; and the second primer comprises a first region and a second region, wherein the second region of the second primer is complementary to a sequence in the PCR amplification reaction product second strand which is complementary to the second portion of the polynucleotide template, the first region of the second primer is complementary to the first region of the first primer, and the first region of the second primer is complementary to the third portion of the polynucleotide template.

In embodiments, in a method or composition provided herein involving a polynucleotide template comprising a first portion and a second portion, the first portion and second portion of the polynucleotide template are each between 6 and 30 nucleotides in length.

In embodiments, in a method or composition provided herein involving a polynucleotide template comprising a third portion, the third portion of the polynucleotide template is between 4 and 14 nucleotides in length.

In embodiments, in a method or composition provided herein involving amplifying a polynucleotide template in a non-thermocycling reaction mixture, the number of copies of the polynucleotide template in the non-thermocycling reaction mixture is increased at least 10-fold within 60 minutes of initiation of the method.

In embodiments, in a method or composition provided herein involving amplifying a polynucleotide template in a non-thermocycling reaction mixture, a concatemer strand comprising at least three copies of the polynucleotide template is generated during the incubation of the non-thermocycling reaction mixture.

In embodiments, provided herein is a vessel comprising therein any one or more components of a reaction mixture described herein.

In embodiments, provided herein is a kit comprising therein any one or more components of a reaction mixture described herein. Optionally, in embodiments provided herein involving a kit, the components of the kit may be distributed between at least two separate fluidically isolated containers.

BRIEF DESCRIPTION OF THE DRAWINGS

In the drawings:

FIG. 1B is a schematic depicting features of an exemplary component of a method provided herein.

FIG. 1C is a schematic depicting features of an exemplary component of a method provided herein.

Figure 1A:
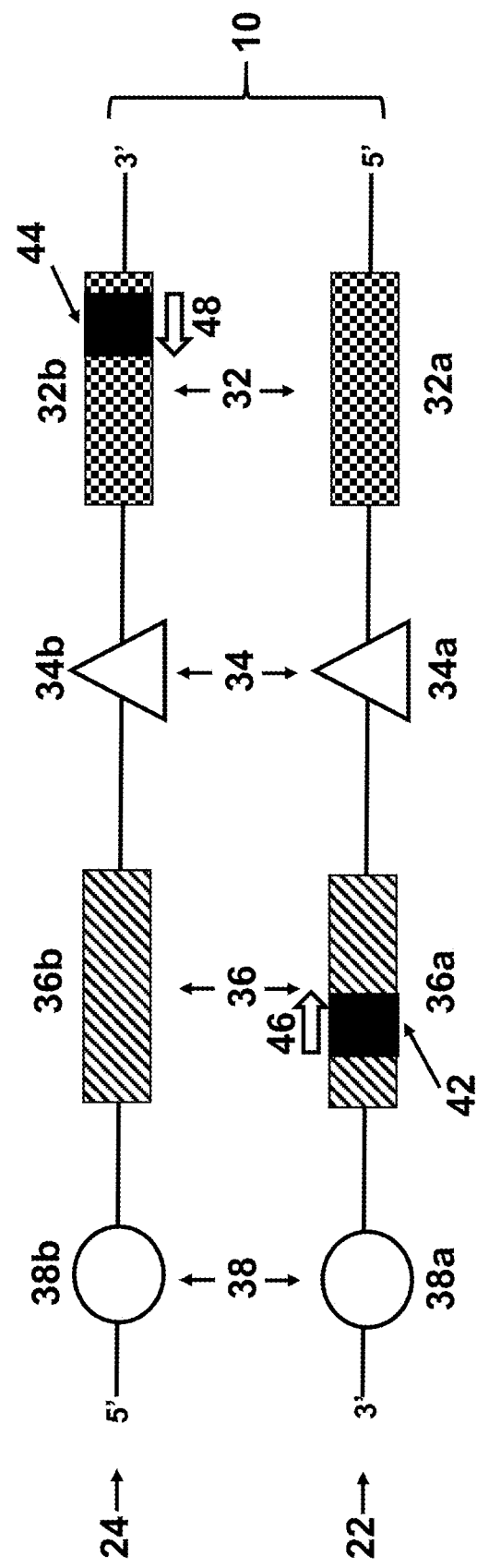
FIG. 1A is a schematic depicting features of an exemplary component of a method provided herein.

It is noted that the drawings and elements therein are not necessarily drawn to shape or scale. For example, the shape or scale of elements of the drawings may be simplified or modified for ease or clarity of presentation. It should further be understood that the drawings and elements therein are for exemplary illustrative purposes only, and not be construed as limiting in any way.

DETAILED DESCRIPTION

Provided herein are methods and compositions relating to the identification of genetic-related information. In embodiments, improved reagents and methods for assessing integrated genes in host genetic material are provided. For example, improved reagents and methods for MRSA detection are provided. In embodiments, improved reagents and methods for assessing whether at least a first genetic element and a second genetic element are both on a common nucleic acid molecule are provided. In such embodiments, the first genetic element and the second genetic element may be separated from each other on the common nucleic acid molecule by a large number of nucleotides. In other embodiments, improved reagents and methods for assessing SNPs and point mutations are provided. For example, improved reagents and methods for assessing the Q80 polymorphism in the Hepatitis C NS3 gene are provided. Various features described herein may be applied to any of the particular embodiments set forth below or for any other types systems for or involving the identification of genetic-related information. Systems and methods described herein may be applied as a stand-alone system or method, or as part of an integrated system or method. It shall be understood that different aspects of the disclosed systems and methods can be appreciated individually, collectively, or in combination with each other.

In embodiments, provided herein are systems, compositions, and methods for MRSA detection. Prior methods for MRSA detection typically separately test a sample for the mecA gene and for genetic material from the S. aureus chromosome. If both the mecA gene and S. aureus genetic material are found in the sample, a presumptive conclusion is made that MRSA is present. However, this conclusion might not be accurate, because the mecA gene can exist outside of S. aureus (as part of the SCCmec, which is transferable between organisms). Thus, a sample that contains both the mecA gene and S. aureus might not actually contain MRSA bacteria; instead, it may contain non-MRSA S. aureus bacteria, and a different bacteria or free genetic element which contains the mecA gene. This situation thus may give rise to a false-positive identification of MRSA in a sample.

Embodiments of methods and compositions provided herein address the above problem, and provide methods and compositions for identifying the mecA gene in a S. aureus chromosome (and thus, true MRSA).

One approach to identifying a mecA gene in a S. aureus chromosome might be to perform, for example, polymerase chain reaction (PCR), where the PCR reaction would contain a sample which might contain MRSA bacteria or MRSA genetic material, and wherein one of the primers for the PCR reaction would anneal to portion of the mecA gene and the other primer for the PCR reaction would anneal to a portion of the S. aureus chromosome. If such a PCR reaction yielded a reaction product, it would indicate that both the mecA gene and genetic material from the S. aureus chromosome were on the same DNA strand (and thus, that the sample contained true MRSA bacteria). However, typically this approach is not effective, because in most MRSA bacteria, the mecA gene is many thousands of nucleotides away from genetic material of the S. aureus chromosome. This is due to the fact that in MRSA, the mecA gene is integrated into the S. aureus chromosome as part of the SCCmec, and the mecA gene is typically in an inner portion of the SCCmec, surrounded on both sides by thousands of additional nucleic acids of the SCCmec insert. The relatively large nucleotide distance between the mecA gene and the S. aureus chromosome in most MRSA strains generally results in the poor performance of traditional PCR reactions as described above (e.g. with one primer annealing to a portion of the mecA gene and the other primer annealing to a portion of the *S. aureus* chromosome), as traditional PCR (e.g. using Taq polymerase) and many other nucleic acid amplification techniques are not very effective at amplifying relatively long nucleotide sequences (e.g. over 3000, 4000, or 5000 nucleotides in length).

SCCmec types are described, for instance, in Antimicrob. Agents Chemother. December 2009 vol. 53 no. 12, pages 4961-4967; Methods Mol Biol. 2014; 1085:131-48, and Methods Mol Biol. 2007; 391:87-102, each of which is hereby incorporated by reference in its entirety for all purposes. Typically, the mecA gene when present in a *S. aureus* chromosome is separated from *S. aureus* genetic material by thousands or even tens of thousands of nucleotides.

In embodiments, provided herein are improved methods and compositions for identifying a mecA gene which has been integrated into a *S. aureus* chromosome.

In embodiments, methods provided herein comprise at least two steps: 1) a step to generate a nucleic acid strand wherein at least a portion of the mecA gene and the *S. aureus* chromosome are in close physical proximity to each other within the strand; and 2) a step to perform a nucleic acid amplification method using at least a first primer, a second primer and the nucleic acid strand of step 1), wherein the first primer anneals to a portion of the mecA gene and the second primer anneals to a portion of the *S. aureus* chromosome, and where an amplification product is generated which includes portions of both the mecA gene and the *S. aureus* chromosome.

Embodiments of systems and methods provided herein may be described as follows. A *S. aureus* chromosome or portion thereof containing a SCCmec cassette containing a mecA gene may be provided (optionally referred to herein as a "MRSA chromosome"). The MRSA chromosome may be incubated with a first primer and a second primer, wherein the first primer is complementary to a portion of the mecA gene (or, optionally, other element of the SCCmec cassette), and the second primer is complementary to a portion of the *S. aureus* chromosome. In addition, one or both of the primers is phosphorylated at the 5' end. The MRSA chromosome is incubated in a first amplification reaction with a DNA polymerase having high processivity. An exemplary DNA polymerase with high processivity is phi29 polymerase. The first amplification reaction may be, for instance, a polymerase chain reaction (PCR reaction) or an isothermal amplification reaction. By use of a DNA polymerase with high processivity, at least a small amount of an amplification product may be generated. The amplification product from this reaction will contain both *S. aureus* and mecA genetic material, but typically, only a small amount of amplified material will be generated from this amplification reaction. This amplified material is generally difficult to detect, due to the small amount generated. Accordingly, the amplified material is then incubated with a DNA ligase, which can ligate these amplification products together (in either intra-strand or inter-strand ligations) due to the phosphate groups on the 5' end of the primers used for the amplification reaction. Incubation of the amplified material from the first amplification reaction with a ligase may result in one or both of two general types of ligation products: a) concatemers formed by the end-to-end ligation of two or more amplification products from the first amplification reaction; or b) circularized products formed by the ligation of one end of an amplification product from the first amplification reaction to the other end of the same amplification product. With both types of ligation products, the mecA gene is brought into close physical proximity with *S. aureus* genetic material (e.g. to the gene attR or orfX). Accordingly, in embodiments, both types of ligation products are suitable templates for nucleic acid amplification methods which are most effective at amplification of relatively small amplicons (e.g. 2000 nucleotides or less). Thus, the next step of a method provided herein involves using one or both of the ligation products for a second nucleic acid amplification step. This second nucleic acid amplification step may use at least a first primer which anneals to a portion of the mecA gene (or optionally, another portion of the SCCmec cassette), and a second primer which anneals to *S. aureus* genetic material. Various nucleic acid amplification methods may be used for the second nucleic acid amplification step, such as PCR or an amplification method as described in PCT/US14/56151, filed Sep. 17, 2014, which is hereby incorporated by reference in its entirety for all purposes. In embodiments, the first primer and second primer of the second nucleic acid amplification step are different than the first primer and second primer of the first nucleic acid amplification step. In embodiments, the first primer and second primer of the second nucleic acid amplification step have an opposite orientation as compared to the first primer and second primer of the first nucleic acid amplification step. In embodiments, the first primer and second primer of the second nucleic acid amplification step are the same as the first primer and second primer of the first nucleic acid amplification step.

Embodiments of systems and methods provided herein may be described with reference to FIG. 1A-1E. In embodiments, the compositions and methods described in and relating to FIGS. 1A-1E may be referred to herein as for "genetic element analysis". A double-stranded nucleic acid molecule 10 may be provided. The double-stranded nucleic acid molecule 10 comprises a first strand 22 and a second strand 24.

The double-stranded nucleic acid 10 may be of any suitable shape and conformation. For example, although FIG. 1 depicts the double-stranded nucleic acid 10 as a linear double-stranded nucleic acid, the double-stranded nucleic acid 10 may alternatively, for example, be part of or the entirety of a circular double-stranded nucleic acid. A circular double-stranded nucleic acid will not have a free 5' or 3' end on either strand of the double-stranded nucleic acid (due to its circular shape). In addition, the double-stranded nucleic acid 10 may be the entirety of a nucleic acid molecule, or it may be only a part of a larger double-stranded nucleic acid.

The double-stranded nucleic acid 10 may be provided from a wide range of sources. For example, the double-stranded nucleic acid 10 may be in or prepared from a sample obtained from a subject, it may be directly obtained from a cultured microorganism, or it may be chemically synthesized.

Within the double-stranded nucleic acid 10, there may be one or more different genetic elements 32, 34, 36, 38. For instance, within the double-stranded nucleic acid 10, there may be at least 1, 2, 3, 4, 5, 6, 7, 8, 9, 10, 15, 20, 25, 50, 100, or more different genetic elements. As used herein, a "genetic element" refers to any identifiable region of interest of a nucleic acid molecule, such as a gene sequence, a promoter sequence, enhancer sequence, intron, exon, etc. A genetic element typically contains two complementary sequences, in which one of the sequences of the genetic element is on the first strand 22 and the other sequence of the genetic element is on the second strand 24, and wherein the sequence of the element on the first strand 22 and the sequence of the element on the second strand 24 are complementary per Watson-Crick base-pairing rules (A with T; C with G). Typically, the complementary sequence on the first strand and the complementary sequence on the second strand contain the same number of nucleotides. Also, as used herein, for any given genetic element, the sequence of the element on the first strand in the 5' to 3' direction may be referred to as the "first complementary sequence" and the sequence of that element on the second strand in the 5' to 3' direction may be referred to as the "second complementary sequence". Accordingly, for example, in situations herein in which a double-stranded nucleic acid molecule contains, for example, a first genetic element, a second genetic element, and a third genetic element, it may be described that the first strand of the double-stranded nucleic acid molecule contains a "first genetic element first complementary sequence", a "second genetic element first complementary sequence", and a "third genetic element first complementary sequence", wherein the "first genetic element first complementary sequence" is the first complementary sequence of the first genetic element, the "second genetic element first complementary sequence" is the first complementary sequence of the second genetic element, and the "third genetic element first complementary sequence" is the first complementary sequence of the third genetic element. Similarly, it may be described that the second strand of the double-stranded nucleic acid molecule contains a "first genetic element second complementary sequence", a "second genetic element second complementary sequence", and a "third genetic element second complementary sequence", wherein the "first genetic element second complementary sequence" is the second complementary sequence of the first genetic element, the "second genetic element second complementary sequence" is the second complementary sequence of the second genetic element, and the "third genetic element second complementary sequence" is the second complementary sequence of the third genetic element. The designation of any given genetic element in a sequence as a "first genetic element", "second genetic element", or "third genetic element", etc. in a sequence is generally arbitrary, and these terms may be used as appropriate to designate different genetic elements of interest on a nucleic acid molecule of interest (as long as the terminology is used consistently for the same genetic elements on a given nucleic acid molecule).

For instance, in FIG. 1, genetic element 32 contains a complementary sequence on the first strand 32a and a complementary sequence on the second strand 32b (also referred to herein as "genetic element 32 first complementary sequence" and "genetic element 32 second complementary sequence", respectively; this naming system also may be used with other genetic elements); the sequence on the first strand 32a and the sequence on the second strand 32b are complementary per Watson-Crick base-pairing rules. Similarly, genetic element 34 contains a complementary sequence on the first strand 34a and a complementary sequence on the second strand 34b; the sequence on the first strand 34a and the sequence on the second strand 34b are complementary per Watson-Crick base-pairing rules. Similarly, genetic element 36 contains a complementary sequence on the first strand 36a and a complementary sequence on the second strand 36b; the sequence on the first strand 36a and the sequence on the second strand 36b are complementary per Watson-Crick base-pairing rules. Similarly, genetic element 38 contains a complementary sequence on the first strand 38a and a complementary sequence on the second strand 38b; the sequence on the first strand 38a and the sequence on the second strand 38b are complementary per Watson-Crick base-pairing rules.

For emphasis, the genetic elements 32, 34, 36, and 38 in FIG. 1A are represented by different geometric shapes (i.e. element 32 is a rectangle, 34 is a triangle, etc.). However, it is important to note that the geometric shapes do not provide details about the characteristic of the genetic element (the shapes are just to assist in outlining various concepts presented in FIGS. 1A-E). Also, while FIG. 1A depicts the complementary sequences 32a, 34a, 36a, 38a, 32b, 34b, 36b, and 38b as being of a different shape than the first strand 22 and the second strand 24 on which the complementary sequences 32a, 34a, 36a, 38a, 32b, 34b, 36b, and 38b reside, these shapes are just for emphasis and the complementary sequences in fact have the same structure as the rest of the portions of the strand.

A genetic element may be of any length of nucleotides. For example, in embodiments, a genetic element may be at least 3, 4, 5, 8, 9, 10, 11, 12, 13, 14, 15, 20, 25, 30, 35, 40, 50, 60, 70, 80, 90, 100, 200, 500, 1000, 2000, or 5000 nucleotides in length. In embodiments, a genetic element may contain no more than 5, 8, 9, 10, 11, 12, 13, 14, 15, 20, 25, 30, 35, 40, 50, 60, 70, 80, 90, 100, 200, 500, 1000, 2000, 5000, or 10,000 nucleotides. In embodiments, a genetic element may contain at least 3, 4, 5, 8, 9, 10, 11, 12, 13, 14, 15, 20, 25, 30, 35, 40, 50, 60, 70, 80, 90, 100, 200, 500, 1000, 2000, or 5000, and no more than 9, 10, 11, 12, 13, 14, 15, 20, 25, 30, 35, 40, 50, 60, 70, 80, 90, 100, 200, 500, 1000, 2000, 5000, or 10,000 nucleotides. Typically, a complementary sequence of a genetic element may be considered to have a 5' end and 3' end, wherein the nucleotides of the complementary sequence include and are between the 5' end and the 3' end of the sequence. For instance, a complementary sequence of a genetic element may have the exemplary sequence in the 5' to 3' direction of: 5' TGGA 3'. In this sequence, the "T" is the nucleotide at the 5' end of the sequence and the "A" is the nucleotide at the 3' end of the sequence.

In a double-stranded nucleic acid molecule containing at least a first genetic element and a second genetic element, the first genetic element and the second genetic element may be separated from each other by any number of nucleotides. For example, in a double-stranded nucleic acid molecule containing at least a first genetic element and a second genetic element, the first genetic element and the second genetic element may be separated from each other by at least 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides, no more than 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides, or at least 5, 6, 7, 8, 9, 10, 11, 12, 13, 14, 15, 20, 25, 30, 35, 40, 50, 60, 70, 80, 90, 100, 200, 500, 1000, 2000, or 5000, and no more than 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides (i.e. there are the aforementioned number of nucleotides between the first genetic element and the second genetic element). In another example, a double-stranded nucleic acid molecule may contain at least a first genetic element and a second genetic element, and on the first strand of the double-stranded nucleic acid molecule, in situations in which the first genetic element first complementary sequence is upstream to the second genetic element first complementary sequence, there may be at least 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides between the 3' end of the first genetic element first complementary sequence and the 5' end of the second genetic element first complementary sequence. In embodiments, a double-stranded nucleic acid molecule may contain at least a first genetic element and a second genetic element, and on the first strand of the double-stranded nucleic acid molecule, in situations in which the first genetic element first complementary sequence is upstream to the second genetic element first complementary sequence, there may be no more than 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides between the 3' end of the first genetic element first complementary sequence and the 5' end of the second genetic element first complementary sequence. In embodiments, a double-stranded nucleic acid molecule may contain at least a first genetic element and a second genetic element, and on the first strand of the double-stranded nucleic acid molecule, in situations in which the first genetic element first complementary sequence is upstream to the second genetic element first complementary sequence, there may be at least 5, 6, 7, 8, 9, 10, 11, 12, 13, 14, 15, 20, 25, 30, 35, 40, 50, 60, 70, 80, 90, 100, 200, 500, 1000, 2000, or 5000, and no more than 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides between the 3' end of the first genetic element first complementary sequence and the 5' end of the second genetic element first complementary sequence. The above statements also apply vice-versa for situations in which the first genetic element first complementary sequence is downstream to the second genetic element first complementary sequence Similarly, in another example, a double-stranded nucleic acid molecule may contain at least a first genetic element and a second genetic element, and on the second strand of the double-stranded nucleic acid molecule, in situations in which the second genetic element second complementary sequence is upstream to the first genetic element second complementary sequence, there may be at least 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides between the 3' end of the second genetic element second complementary sequence and the 5' end of the first genetic element second complementary sequence. In embodiments, a double-stranded nucleic acid molecule may contain at least a first genetic element and a second genetic element, and on the second strand of the double-stranded nucleic acid molecule, in situations in which the second genetic element second complementary sequence is upstream to the first genetic element second complementary sequence, there may be no more than 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides between the 3' end of the second genetic element second complementary sequence and the 5' end of the first genetic element second complementary sequence. In embodiments, a double-stranded nucleic acid molecule may contain at least a first genetic element and a second genetic element, and on the second strand of the double-stranded nucleic acid molecule, in situations in which the second genetic element second complementary sequence is upstream to the first genetic element second complementary sequence, there may be at least 5, 6, 7, 8, 9, 10, 11, 12, 13, 14, 15, 20, 25, 30, 35, 40, 50, 60, 70, 80, 90, 100, 200, 500, 1000, 2000, or 5000, and no more than 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides between the 3' end of the second genetic element second complementary sequence and the 5' end of the first genetic element second complementary sequence.

In embodiments, a first amplification reaction may be performed in order to amplify at least a portion of the double-stranded nucleic acid molecule 10. Frequently, it may be desirable to determine whether a first genetic element of interest and a second genetic element of interest are present in a sample and specifically if they are part of the same double-stranded nucleic acid molecule 10. It may be important to determine whether a first genetic element of interest and a second genetic element of interest are part of the same double-stranded nucleic acid molecule in order to better understand, for example, the genetic characteristics of a pathogen that may be in the sample. For example, it may be of interest to determine whether a particular antibiotic-resistant strain of a particular bacteria is present in a sample from a subject, and this may be determined by identifying, for example, if there is a double-stranded nucleic acid molecule which contains both an antibiotic resistance gene (i.e. a first genetic element) and a gene from a particular species of bacteria (i.e. a second genetic element). Such double-stranded nucleic acid molecules may be formed, for example, when a bacterium acquires an antibiotic-resistance gene and the antibiotic resistance gene is then integrated into a chromosome of the bacterium. An antibiotic resistance gene typically provides resistance against a particular antibiotic or class or antibiotics by encoding a protein which facilitates resistance against that antibiotic or class of antibiotic (e.g. the protein facilitates, for example, chemically deactivating the antibiotic or pumping the antibiotic out of the bacteria).

Thus, in performing a first amplification reaction to amplify at least a portion of the double-stranded nucleic acid molecule 10, it may be desirable to generate an amplification product that contains at least a portion of a first genetic element of interest and at least a portion of a second genetic element of interest. The successful generation of this kind of amplification product (i.e. which contains at least a portion a first genetic element of interest and at least a portion of a second genetic element of interest) from an amplification reaction indicates that there is a template double-stranded nucleic acid molecule 10 in the amplification reaction mixture which contains both the first genetic element of interest and the second genetic element of interest on the same double-stranded nucleic acid molecule. An amplification product from a first nucleic acid amplification provided herein may be referred to herein as a "first amplification reaction product".

In order to perform a first amplification reaction which can potentially generate a first nucleic acid amplification product that contains at least a portion of a first genetic element and at least a portion of a second genetic element (assuming that there is a template double-stranded nucleic acid molecule 10 which contains both the first genetic element of interest and the second genetic element of interest on the same double-stranded nucleic acid molecule in the first amplification reaction mixture), a first primer 46 and a second primer 48 may be provided (a "first amplification reaction first primer" 46 and a "first amplification reaction second primer" 48, respectively) in a first amplification reaction mixture.

The first amplification reaction first primer 46 may have a nucleotide sequence which is complementary to at least a portion of a first genetic element of interest 36, and, in embodiments, specifically to at least a portion of the first complementary sequence 36a of the first genetic element 36. Due to the complementation between the nucleotide sequence of the first amplification reaction first primer 46 and the nucleotide sequence of the at least a portion of the first complementary sequence 36a of the first genetic element 36, the first amplification reaction first primer 46 may anneal to the at least a portion of the first complementary sequence 36a of the first genetic element 36. In the block arrow in FIG. 1A representing the first amplification reaction first primer 46 (and for all other arrows in figures herein), the pointed end of the arrow represents the 3' end of the primer, and the rectangle end of the arrow represents the 5' end of the primer. Thus, the primer will be extended by a polymerase in the direction of the pointed arrow. In FIG. 1A, the portion of the first complementary sequence 36a to which the first amplification reaction first primer 46 is complementary and to which the first amplification reaction first primer 46 can anneal is illustrated with a black square 42. While the portion of the first complementary sequence 36a to which the first amplification reaction first primer 46 is complementary 42 is only a portion of the first complementary sequence 36a in FIG. 1A, it should be understood that the portion of the first complementary sequence 36a to which the first amplification reaction first primer 46 is complementary 42 could alternatively be the entirety of the first complementary sequence 36a, be a different size relative to the first complementary sequence 36a, or be in a different position within the first complementary sequence 36a.

The first amplification reaction second primer 48 may have a nucleotide sequence which is complementary to at least a portion of a second genetic element of interest 32, and, in embodiments, specifically to at least a portion of the second complementary sequence 32b of the second genetic element 32. Due to the complementation between the nucleotide sequence of the first amplification reaction second primer 48 and the nucleotide sequence of the at least a portion of the second complementary sequence 32b of the second genetic element 32, the first amplification reaction second primer 48 may anneal to the at least a portion of the second complementary sequence 32b of the second genetic element 32. In FIG. 1A, the portion of the second complementary sequence 32b to which the first amplification reaction second primer 48 is complementary and to which the first amplification reaction second primer 48 can anneal is illustrated with a black square 44. While the portion of the second complementary sequence 32b to which the first amplification reaction second primer 48 is complementary 44 is only a portion of the second complementary sequence 32b in FIG. 1A, it should be understood that the portion of the second complementary sequence 32b to which the first amplification reaction second primer 48 is complementary 44 could alternatively be the entirety of the second complementary sequence 32b, be a different size relative to the second complementary sequence 32b, or be in a different position within the second complementary sequence 32b.

In embodiments, one or both of the first amplification reaction first primer 46 and the first amplification reaction second primer 48 may be phosphorylated at the 5' end of the primer. In embodiments, the primers may be provided to the first amplification reaction mixture in an already-phosphorylated form. If a primer is not already phosphorylated, it may be treated with a kinase (e.g. T4 polynucleotide kinase) in order to phosphorylate the primer.

The first amplification reaction may utilize any suitable nucleic acid replication technique which involves at least two template-specific primers (e.g. a first primer to anneal to a sequence of the first genetic element and a second primer to anneal to a sequence of the second genetic element). In embodiments, the first nucleic acid replication technique is polymerase chain reaction (PCR). PCR is described in, for example, U.S. Pat. No. 4,683,202, which is hereby incorporated by reference for all purposes. In other embodiments, the first nucleic acid replication technique may be an isothermal amplification reaction. Such isothermal amplifications may use, for instance, phi29 DNA polymerase (or another DNA polymerase that is highly processive and has strand-displacement activity), and may be performed by first heat-denaturing the common double-stranded nucleic acid molecule (in order to permit the first primer and second primer to anneal to their complementary sequences), and then permitting the primers to be extended and copies thereof to be generated under isothermal conditions (typically at a temperature between 40 and 65 C). The first amplification reaction may generate a first amplification reaction product, which contains at least a portion of the first genetic element and at least a portion of the second genetic element.

The first amplification reaction mixture includes a nucleic acid polymerase (e.g. a DNA polymerase). A nucleic acid polymerase used in the first amplification reaction may be a DNA polymerase which has a relatively high processivity (i.e. which is capable of readily amplifying templates of at least, for example, 3000 nucleotides in length). DNA polymerases with high processivity include, for example, LongAmp® Taq DNA Polymerase (New England BioLabs, Inc.; it is a blend of Taq and DeepVentR™ DNA polymerases), Q5® High-Fidelity DNA Polymerase (New England BioLabs, Inc.), Phusion® High-Fidelity DNA Polymerase (New England BioLabs, Inc.), HOTSTAR HIGHFIDELITY DNA POLYMERASE (Qiagen), and phi29 DNA polymerase. In addition, a nucleic acid polymerase used in the first amplification reaction may be a DNA polymerase which has strand-displacement activity.

In some embodiments, methods and steps thereof provided herein for amplification reactions include or are performed under conditions sufficient to support polymerase-based nucleic acid synthesis. Example conditions for polymerase-based nucleic acid synthesis are known in the art and are provided, for example, in Molecular Cloning: A Laboratory Manual, M. R. Green and J. Sambrook, Cold Spring Harbor Laboratory Press (2012), which is herein incorporated by reference in its entirety. Non-limiting components for a polymerase-based nucleic acid synthesis reaction may include one or more of: polymerase enzyme (at a concentration between, for example, 0.01 and 10 units enzyme per 50 microliters reaction volume, or any range therein including, for example, between 0.01-1, 0.1-10, 0.1-5, 0.5-10, 0.5-5, 0.5-2, 1-10, or 1-5 units enzyme per 50 microliters reaction volume, where 1 unit of enzyme will incorporate 15 nmol of dNTPs into polymerization product in 30 minutes at 75 C); template (at a concentration of at least, for example, 1, 10, 100, 1,000, 10,000, or 100,000 copies per reaction); primer (at a concentration between, for example, 0.01 and 10 micromolar, or any range therein including, for example, between 0.01-1, 0.1-10, 0.1-5, 0.5-5, or 0.5-2 micromolar); dNTPs (e.g. dATP, dTTP, dGTP, and dCTP, at a concentration between, for example, 50 and 500 micromolar each of dATP, dTTP, dGTP, and dCTP, or any range therein including, for example, between 50-350, 100-500, 100-300, 200-500, or 300-400 micromolar each of dATP, dTTP, dGTP, and dCTP); salt (e.g. KCl or potassium acetate, at a concentration between, for example, 1 and 200 millimolar, or any range therein including, for example, between 1-100, 1-50, 1-20, 1-10, 10-20, 10-50, or 10-200 millimolar); buffer (e.g. Tris-HCl or Tris-acetate, pH 7.8-8.5, at a concentration between, for example, 1 and 100 millimolar, or any range therein including, for example, between 1-50, 1-20, 1-10, 1-5, 10-100, 20-100, or 50-100 millimolar); and magnesium ions (at a concentration between, for example 0.1 and 10 millimolar, or any range therein, including, for example, between 0.1-5, 0.1-1, 0.5-10, 0.5-5, or 0.5-2.5 millimolar). Additional non-limiting components for a polymerase-based nucleic acid synthesis reaction may increase the speed of the reaction, increase the fidelity of the reaction, or increase the stability of enzymes or DNA in the reaction, and may include one or more of: gelatin (at a concentration between, for example, 0.0001% and 0.1% w/v), BSA (at a concentration between, for example, 0.01 and 1 microgram per microliter), sucrose (at a concentration between, for example 0.01 molar and 0.8 molar), trehalose (at a concentration between, for example 0.01 molar and 0.8 molar), DMSO (at a concentration between, for example, 0.01 and 10% v/v), betaine (at a concentration between, for example, 0.1 and 10 molar), formamide (at a concentration between, for example, 0.1 and 10% v/v), glycerol (at a concentration between, for example, 0.1 and 20% v/v), polyethylene glycol (at a concentration between, for example, 0.1 and 20% v/v), non-ionic detergents [e.g. NP-40 (at a concentration between, for example, 0.01 and 1% v/v), Tween-20 (at a concentration between, for example, 0.01 and 1% v/v), or Triton X-100 (at a concentration between, for example, 0.01 and 1% v/v)], ammonium ions [e.g. ammonium sulfate (at a concentration between, for example, 1 and 100 millimolar)], and EDTA (at a concentration between, for example, 0.001 and 0.1 millimolar). Other reagents may also be present in a polymerase-based nucleic acid synthesis reaction provided herein. For example, reagents sufficient to synthesize RNA reaction products or reaction products containing non-standard nucleotides may be used. Conditions sufficient to support polymerase-based nucleic acid synthesis may include a variety of temperatures and pH values. For example, the pH of a polymerase-based nucleic acid synthesis reaction may be between, for example pH 6.0 and pH 10.0, such as 6.5, 7, 7.5, 7.8, 7.9, 8, 8.1, 8.2, 8.5, 9, or 9.5. The temperature of a polymerase-based nucleic acid synthesis reaction may be constant or varied. A constant temperature may be between, for example, 10 C and 95 C, such as 20, 25, 30, 35, 37, 40, 42, 45, 50, 55, 60, 65, 70, 75, 80, or 85 C. A varied temperature may be two or more different temperatures between, for example, 10 C and 95 C, such as two or more temperatures selected from 20, 25, 30, 35, 37, 40, 42, 45, 50, 55, 60, 65, 70, 75, 80, or 85 C. In some embodiments, a varied temperature may vary cyclically (e.g. in a PCR reaction, cyclically between such as 94-98 C, then 50-65 C, then 72-80, then back to 94-98 C and continuing the cycle for about 10-50 cycling rounds) Any of the above reagents may be provided in an amplification reaction mixture described herein; similarly, any reagent described as being in an "amplification reaction" described herein may also be described as being in a corresponding "amplification reaction mixture".

FIG. 1B depicts an exemplary first amplification reaction product 50. The first amplification reaction product 50 contains a first amplification reaction product first strand 52 and a first amplification reaction product second strand 54. The first amplification reaction product first strand 52 and the first amplification reaction product second strand 54 are shorter in nucleotide length than the first 22 and second strand 24 of the common double-stranded nucleic acid molecule 10, as only the nucleotides between and including the nucleotides to which the first amplification reaction first primer 46 and the first amplification reaction second primer 48 anneal are amplified. As depicted in FIG. 1B, the first amplification product 50 contains genetic elements 32, 34, and 36. Also, it is noted that although FIG. 1B labels certain features as genetic elements 32 and 36 (and thus suggest that these features are the same as elements 32 and 36 as in FIG. 1A), the elements 32 and 36 in FIG. 1B (and subsequent figures) may be slightly different than in FIG. 1A. Specifically, these elements might not contain all of the nucleotides that are present in these elements in FIG. 1A. This can occur, for example, if the portion of the first complementary sequence 36a to which the first amplification reaction first primer 46 is complementary 42 is in the middle of the first complementary sequence 36a (rather than at the end), such that only a portion of the first genetic element is amplified in the first amplification reaction (or correspondingly for the first amplification reaction second primer and the second genetic element). Nonetheless, the features labeled as features 32 and 36 in FIG. 1B and subsequent figures in FIG. 1 will have nucleotides sequence closely related to that of features 32 and 36 in FIG. 1A, respectively—the nucleotide sequences in FIG. 1B and subsequent figures may just be shorter in length than in FIG. 1A. As shown in FIG. 1B, a first amplification reaction product 50 may have a double-stranded, linear configuration.

In embodiments, in a first amplification reaction product which contains at least a portion of a first genetic element of interest and at least a portion of a second genetic element of interest, there are at least 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides, no more than 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides, or at least 5, 6, 7, 8, 9, 10, 11, 12, 13, 14, 15, 20, 25, 30, 35, 40, 50, 60, 70, 80, 90, 100, 200, 500, 1000, 2000, or 5000, and no more than 5, 6, 7, 8, 9, 10, 11, 12, 13, 14, 15, 20, 25, 30, 35, 40, 50, 60, 70, 80, 90, 100, 200, 500, 1000, 2000, 5000, 10,000, 20,000, 30,000, 40,000, 50,000, 60,000, 70,000, or 100,000 nucleotides between the 3' end of the first genetic element and the 5' start of the second genetic element (or vice-versa).

In embodiments, a first amplification reaction product may be phosphorylated at the 5' end of one or both of the first amplification reaction product first strand 52 or the first amplification reaction product second strand 54. A phosphorylated first amplification reaction product may be generated by using phosphorylated first and second primers in the first amplification reaction, or a first amplification reaction product may be phosphorylated once it is generated. In either case, the respective molecule may be phosphorylated by methods known in the art (e.g. with T4 polynucleotide kinase).

A first amplification reaction product may be provided in a ligation reaction mixture, in which a ligation reaction occurs. The ligation reaction mixture contains a DNA ligase (e.g. T4 DNA ligase). In the ligation reaction, a terminal 5' phosphate of a polynucleotide (e.g. DNA or RNA) strand forms a covalent phosphodiester bond with a 3' OH group of a polynucleotide strand. In a ligation reaction, the 5' phosphate of a polynucleotide strand may link with a 3' OH group of the same strand (i.e. an intra-strand ligation), or the 5' phosphate may link with a 3' OH group of a different strand (i.e. an inter-strand ligation). As depicted in FIG. 1C, in embodiments provided herein, a phosphorylated first amplification reaction product in a ligation reaction mixture may yield a circular ligation product 60. In the circular ligation product 60, there is a circular ligation product first strand 62 and a circular ligation product second strand 64, which have been formed from the first amplification reaction product first strand 52 and the first amplification reaction product second strand 54, respectively (i.e. by ligating the 5' end of the first amplification reaction product first strand 52 to the 3' end of the same strand, to form the circular ligation product first strand 62 and by ligating the 5' end of the first amplification reaction product second strand 54 to the 3' end of the same strand, to form the circular ligation product second strand 64). As shown in FIG. 1C, in the circular ligation product 60, on the first strand 62, the complementary sequence 32a of genetic element 32 is adjacent to the complementary sequence 36a of genetic element 36. Also, on the circular ligation product second strand 64, the complementary sequence 32b of genetic element 32 is adjacent to the complementary sequence 36b of genetic element 36. Thus, the formation of the circular ligation product 60 brings genetic element 32 much closer to genetic element 36 in the circular ligation product 60 than these genetic elements occur in relation to each other in the common double-stranded nucleic acid molecule 10.

In embodiments, a phosphorylated first amplification reaction product in a ligation reaction mixture may yield an end-to-end ligation product (in addition to or alternatively to a circular ligation product 60). In an end-to-end ligation product, a first copy of a phosphorylated first amplification reaction product is ligated end-to-end with a second copy of the phosphorylated first amplification reaction product (e.g. in embodiments, the 3' end of the first strand of a first copy of the first amplification reaction product is ligated to the 5' end of the first strand of a second copy of the first amplification reaction product, and the 3' end of the second strand of the second copy of the first amplification reaction product is ligated to the 5' end of the second strand of the first copy of the first amplification reaction product, such that an end-to-end ligation product is formed which contains an end-to-end ligation product first strand and an end-to-end ligation product second strand, and the end-to-end ligation product first strand contains at least two copies of the first strand of the first amplification reaction product and the end-to-end ligation product second strand contains at least two copies of the second strand of the first amplification reaction product). In an end-to-end ligation product, a copy of genetic element 32 may be brought much closer to a copy of genetic element 36 than these genetic elements occur in relation to each other in the common double-stranded nucleic acid molecule 10.

Figure 1E:
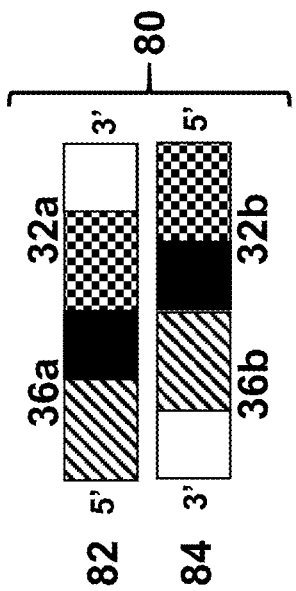
FIG. 1E is a schematic depicting features of an exemplary component of a method provided herein.
Figure 1D:
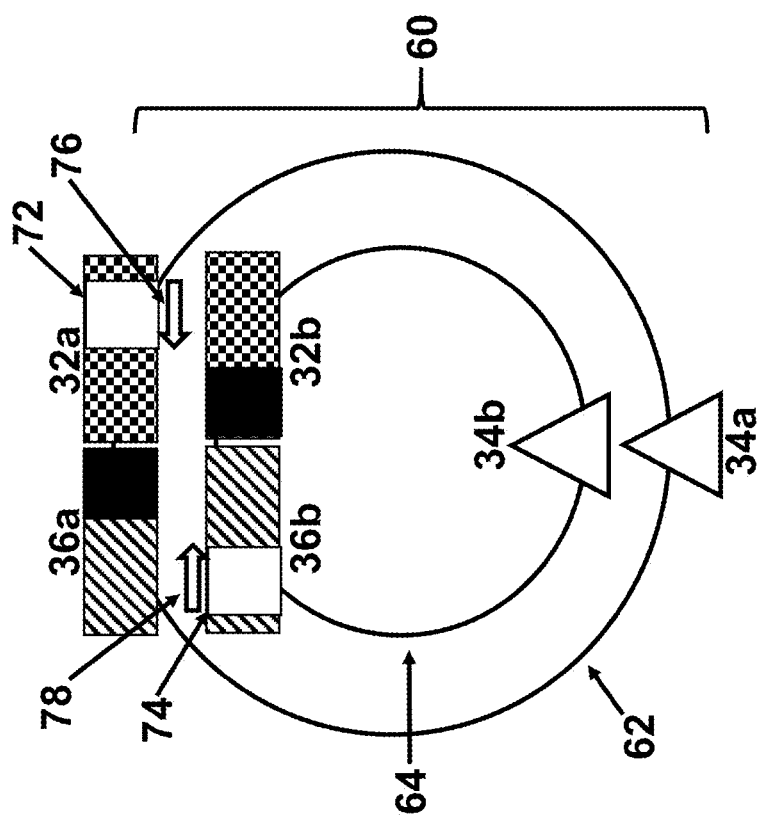
FIG. 1D is a schematic depicting features of an exemplary component of a method provided herein.

One or both of a circular ligation product or an end-to-end ligation product may be provided to a second amplification reaction mixture. FIG. 1D depicts a circular ligation product 60 in a second amplification reaction. In a second amplification reaction mixture, a second amplification reaction first primer 76 and a second amplification reaction second primer 78 are provided. At least a region of the second amplification reaction first primer 76 is complementary to and anneals to a portion 72 of genetic element 32 (in this example, the second genetic element of interest) first complementary sequence 32a, and at least a region of the second amplification reaction second primer 78 is complementary to and anneals to a portion 74 of genetic element 36 (in this example, the first genetic element of interest) second complementary sequence 36b. As indicated by the directionality of the arrows representing the second amplification reaction first primer 76 and the second amplification reaction second primer 78, the extension products of the primers in the second amplification reaction may be synthesized in a direction opposite that of the direction of synthesis of the extension product of primers in the first amplification reaction. The directionality of the second amplification reaction first primer 76 and the second amplification reaction second primer 78 in the second amplification reaction permits the rapid amplification of the first genetic element and the second genetic element, without the need of amplifying intervening nucleotide sequences (or additional genetic elements therein), thus permitting a robust amplification of and detection of the first genetic element.

A second amplification reaction may utilize any suitable nucleic acid replication technique which involves at least two template-specific primers (e.g. a first primer to anneal to a sequence of the first genetic element and a second primer to anneal to a sequence of the second genetic element). Exemplary suitable nucleic acid replication techniques that may be used for the second amplification reaction include, for instance, PCR or an amplification method as described in PCT/US14/56151, which is hereby incorporated by references for all purposes. PCT/US14/56151 describes methods and compositions for nucleic acid replication. In embodiments, the methods of PCT/US14/56151 can be performed without thermocycling. In embodiments, a method of PCT/US14/56151 may involve a first primer and a second primer. In embodiments, the first primer of a method of PCT/US14/56151 contains a first region and a second region, wherein the first region comprises a 5' end of the primer, the second region comprises a 3' end of the primer, and the second region is complementary to a least a portion of a first strand of a double-stranded nucleic acid template (i.e. a double-stranded nucleic acid molecule). In embodiments, the second primer of a method of PCT/US14/56151 contains a first region and a second region, wherein the first region comprises a 5' end of the primer and is complementary to the first region of the first primer, the second region comprises a 3' end of the primer, and wherein the second region is complementary to a least a portion of a second strand of the double-stranded nucleic acid template. In embodiments, the second region of a first primer of a method of PCT/US14/56151 may anneal to a first complementary sequence of an element as provided in methods herein in the same way as a first primer in methods provided herein, and the second region of a second primer of a method of PCT/US14/56151 may anneal to a second complementary sequence of an element as provided in methods herein in the same way as a second primer in methods provided herein. Methods and compositions of PCT/US14/56151 are described in additional detail elsewhere herein.

The second amplification reaction may generate a second amplification reaction product 80, which contains at least a portion of the first genetic element and at least a portion of the second genetic element. In embodiments, the second amplification reaction product 80 may have a double-stranded, linear configuration. As depicted in FIG. 1E, the second amplification reaction product 80 contains a second amplification reaction product first strand 82 and a second amplification reaction product second strand 84. The second amplification reaction product first strand 82 contains the first complementary sequence 36a of the first genetic element 36 and the first complementary sequence 32a of the second genetic element 32. The second amplification reaction product second strand 84 contains the second complementary sequence 36b of the first genetic element 36 and the second complementary sequence 32b of the second genetic element 32. In embodiments, the second amplification reaction product 80 may form concatemers containing two or more copies of the first genetic element 36 and the second genetic element 32, if, for example, the second amplification reaction is performed as a method described in PCT/US14/56151.

The second amplification reaction product 80 may be detected by methods known if the art for the detection of nucleic acids, and as described elsewhere herein.

In an example, a method provided herein for the detection of two genetic elements on a common double-stranded nucleic acid molecule may be performed as follows. In this example, the sequences of the primers and the genetic elements are shorter (i.e. have fewer nucleotides) than is typical for a method provided herein. However, the sequences in this example are sufficient to provide information about exemplary steps of an embodiment of a method provided herein. In this example, a first genetic element and a second genetic element are of interest. The first complementary sequence of the first genetic element is: 5' AAT 3' and the second complementary sequence of the first genetic element is: 5' ATT 3'. The first complementary sequence of the second genetic element is: 5' TTG 3' and the second complementary sequence of the second genetic element is 5' CAA 3'. The first genetic element and the second genetic element are present on a common double-stranded nucleic acid molecule. As used herein, description of two or more elements as being on a "common" molecule indicates that the elements are part of the same contiguous molecule (i.e. the same single or double-stranded DNA molecule). The nucleotide sequence of the first strand of the common double-stranded nucleic acid molecule is: 5' TTGXAAT 3', where X is any number and sequence of nucleotides. For example, X may contain at least 100, 500, 1000, 2000, 3000, 4000, 5000, or 10,000 nucleotides. The nucleotide sequence of the second strand of the double-stranded nucleic acid molecule is: 5' ATTX'CAA 3', where X' is a number and sequence of nucleotides complementary to the sequence of X. In the first amplification reaction mixture, a first amplification reaction first primer and a first amplification reaction second primer are provided. The nucleotide sequence of the first amplification reaction first primer is: 5' ATT 3'. The nucleotide sequence of the first amplification reaction second primer is: 5' TTG 3'. In the first amplification reaction mixture, a first amplification reaction product is generated. The first amplification reaction product contains a first amplification reaction product first strand and a first amplification reaction product second strand. The nucleotide sequence of the first amplification reaction product first strand is: 5' TTGXAAT 3', where X is any number and sequence of nucleotides. The nucleotide sequence of the first amplification reaction product second strand is: 5' ATTX'CAA 3', where X' is a number and sequence of nucleotides complementary to the sequence of X. (While in this example, the first amplification reaction product is the same size as the common double-stranded nucleic acid molecule, typically, in methods provided herein, the first amplification reaction product is shorter in length than the common double-stranded nucleic acid molecule.) In the ligation reaction mixture, a circular ligation product is formed from the first amplification reaction product, in which the circular ligation product first strand has a nucleotide sequence of: 5' TTGXAAT 3', and wherein the 5' T and 3' T are covalently linked are part of a circular polynucleotide. The circular ligation product second strand has a nucleotide sequence of: 5' ATTX'CAA 3', and wherein the 5' A and 3' A are covalently linked are part of a circular polynucleotide. In the second amplification reaction mixture, a second amplification reaction first primer and a second amplification reaction second primer are provided. The nucleotide sequence of the second amplification reaction first primer is: 5' CAA 3'. The nucleotide sequence of the second amplification reaction second primer is: 5' AAT 3'. In the second amplification reaction mixture, a second amplification reaction product is generated. The second amplification reaction product contains a second amplification reaction product first strand and a second amplification reaction product second strand. The nucleotide sequence of the second amplification reaction product first strand is: 5' AATTTG 3'. The nucleotide sequence of the second amplification reaction product second strand is: 5' CAAATT 3'.

In embodiments, all of the steps of methods provided herein may be permitted to occur simultaneously in the same vessel (e.g. all reagents for methods provided herein may be provided in the same vessel at the same time). Also, provided herein are kits containing reagents for methods provided herein.

In addition to being used for the detection of true MRSA bacteria, the method provided herein may also be used for the detection of other genetic elements in other species or molecules, in which, for example, there are two or more genetic elements which may be on a common nucleic acid strand or part of a common molecule, but for which the elements are separated from each other by a large nucleotide distance. A general approach as provided herein (i.e. to perform a first amplification reaction, followed by a ligation reaction, followed by a second amplification reaction) may be used for a wide range of genetic elements which present a similar structural problem.

In addition, in embodiments, the first amplification reaction provided herein may be omitted, if multiple copies of a molecule containing genetic elements of interest are already present, and such molecules may be ligated together to form structures in which the elements of interest may be readily amplified by, for example, as PCR or an amplification method as described in PCT/US14/56151.

In embodiments, provided herein are compositions and methods for evaluating a SNP, mutation, or other nucleotide of interest in a target sequence. In some situations, a target sequence may have multiple different polymorphisms which surround the position of the nucleotide of interest. For example, the nucleotide of interest may be located in the $60^{th}$ nucleotide position of a target sequence of 150 nucleotides (with the 5' most nucleotide being in the first position, the nucleotide next to the 5' most nucleotide being in the second position, etc.), and other nucleotides in the target sequence may also frequently be variable (e.g. the $49^{th}$, $51^{st}$, $57^{th}$ nucleotide position may also frequently have variant nucleotides/be SNP sites).

In embodiments, a nucleotide of interest may be evaluated through use of a method for SNP detection as provided in PCT/US14/56151, filed Sep. 17, 2014, which is hereby incorporated by reference in its entirety for all purposes. In such a method, a primer pair is used to amplify a target nucleic acid containing the nucleotide of interest, wherein each primer contains a tail/first region and a template-binding/second region. In embodiments, the tail of the/first region of the second primer of the primer pair is complementary to a portion of the target nucleic acid including the nucleotide of interest. In a method as disclosed in PCT/US14/56151, the identity of a nucleotide of interest may be determined, for example, by comparing the rate or amount of amplification of a target nucleic acid containing the nucleotide of interest by one or more primer pairs having slightly different nucleotide sequences in the first/tail region of the primer (typically by just a single nucleotide difference between the primer pairs).

However, in some situations, it may be difficult to perform a method for SNP detection as provided in PCT/US14/56151, if there is a lot of sequence variance in the target nucleic acid one or more positions near the nucleotide of interest. Such positions, for example, may be in the region corresponding to the template-binding regions of the first and/or second primer. If the primers as described in PCT/US14/56151 for SNP detection are not able to readily bind to a target nucleic acid sequence, the method disclosed therein may not be effective for SNP detection.

Accordingly, provided herein are compositions and methods which facilitate the identification of SNPs or other nucleotides of interest. In embodiments, steps and reagents for this type of method may be referred to herein as for "nucleotide analysis". In a first step, a region of a target nucleic acid containing the nucleotide of interest is amplified by a first amplification reaction (such as PCR; also referred to herein as a "PCR amplification reaction"), to generate a PCR amplification reaction product. A PCR amplification reaction may occur in a PCR amplification reaction mixture. In this PCR amplification reaction, relatively long primer pairs (e.g. each primer contains at least 15, 20, 25, 30, 35, 40, 45, 50, 55, 60, 65, 70, 80, 90, or 100 nucleotides) may be used to amplify the target nucleic acid. The long primers may tolerate relatively large amounts of sequence diversity in the template-binding regions (i.e. because the primers are long, they may still anneal to a target sequence, even if multiple nucleotides are mis-matched). Importantly, in the PCR amplification reaction, neither of the primers is to anneal to the exact position of the nucleotide/SNP of interest (i.e. the primers should only anneal to areas near the SNP of interest). This is because with methods provided herein, it is not desirable to change the identity of the nucleotide/SNP of interest (since it is desired to identify the nucleotide/SNP of interest). Once a PCR amplification product is generated in the PCR amplification reaction, the PCR amplification product will have a generally known nucleotide sequence (as a result of knowing the nucleotide sequence of the primers used in the PCR amplification reaction to generate the PCR reaction amplification product). However, the identity of the nucleotide/SNP of interest will still be unknown in the PCR amplification reaction product, since neither of the primers used in the PCR amplification reaction annealed to the location of the nucleotide/SNP of interest. The PCR amplification reaction product may then incubated with primers as provided in PCT/US14/56151 for SNP detection. These primers may be designed to have regions that are complementary to sequences that are known to be present in the PCR amplification reaction product, based on the fact that the PCR amplification reaction product was generated through use of primers of known sequences. The identity of a SNP/nucleotide of interest may then be determined as described in PCT/US14/56151.

Figure 2:
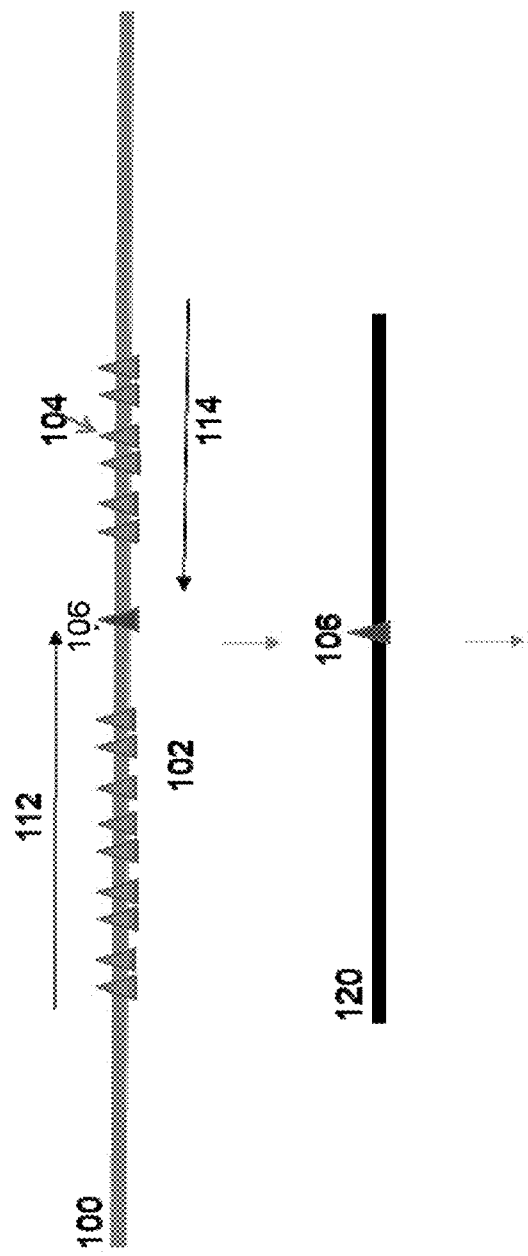
FIG. 2 is a general schematic of steps of a method provided herein.

FIG. 2 provides a general schematic of a method provided herein. A nucleic acid strand 100 containing a target nucleic acid 102 may be provided. The target nucleic acid 102 may contain multiple polymorphisms/variant nucleotides 104. The target nucleic acid 102 also contains a nucleotide/SNP of interest 106. The target nucleic acid is incubated with a PCR amplification reaction first primer 112 and a PCR amplification reaction second primer 114 in a PCR reaction mixture, in order to generate a PCR amplification reaction product 120. The PCR amplification reaction product 120 will have a generally known nucleotide sequence, since it was amplified with the PCR amplification reaction first primer 112 and the PCR amplification reaction second primer 114 (which have known nucleotide sequences). The PCR amplification reaction product 120 is a double-stranded nucleic acid molecule which contains a PCR amplification reaction product first strand and a PCR amplification reaction product second strand. In embodiments, the PCR amplification reaction product first strand may be a copy of a polynucleotide template of interest. During the process of generating the PCR amplification reaction product 120, the multiple polymorphisms/variant nucleotides 104 are replaced by the nucleotides of the first primer 112 and second primer 114. However, the PCR amplification reaction product 120 still has an unknown nucleotide/SNP of interest 106. The PCR amplification reaction product 120 may then be used in a method as described in PCT/US14/56151 for SNP detection.

In embodiments, a PCR amplification reaction used as part of a method for nucleotide analysis may be performed in the same way as a first amplification reaction as provided herein for a genetic element analysis first amplification reaction (e.g. both amplification reactions may be PCR reactions). Similarly, in embodiments, the components of a genetic element analysis first amplification reaction mixture may be the same as the components of a PCR amplification reaction mixture provided herein (taking in to account, for example, differences in primer and template nucleotide sequences and temperature or reagent optimizations). Also, steps and reagents provided herein may be generally referred to with the prefix "genetic element analysis" or "nucleotide analysis", if it is desirable to identify a particular method step or reagent as being associated with the genetic element analysis or nucleotide analysis processes described herein. Alternatively, a method step or reagent provided herein might not be referred to with the prefix "genetic element analysis" or "nucleotide analysis" (e.g. a first primer or first strand), if the context clearly indicates a particular method or, alternatively, if a statement is broadly applicable to various types of primers or method steps (i.e. not just to a specific method or reagent).

In embodiments, methods provided herein may be used to assess a SNP in the polymorphic site Q80K in the Hepatitis C protease gene, NS3. An exemplary primer pair that may be used in a method provided herein for assessing the Q80K site is: First primer (5' to 3' direction): GGAACGAGGAC-CATCGCATCACCCAAGGGTCCTGTTATCCAGATG-TATACCAAT GTAGAC (SEQ ID NO: 1); Second primer (5' to 3' direction): CGCAGGTGCAGGGTGTCAAT-GAGCGGGCACCTTGAGGAGCGGGCCAGCCCACGA GGTCT (SEQ ID NO: 2). Methods provided herein may be used to assess SNPs in many different target nucleic acids, wherein the target nucleic acids have a high level of sequence variability.

In embodiments, all of the steps of methods provided herein may be permitted to occur simultaneously in the same vessel (e.g. all reagents for methods provided herein may be provided in the same vessel at the same time).

In embodiments, a method provided herein may be performed as follows. A polynucleotide template may be amplified in a first amplification reaction, wherein the first amplification reaction is a PCR reaction. In the first amplification reaction, a PCR amplification reaction product may be generated. The PCR amplification reaction product may be a double-stranded nucleic acid molecule comprising a first strand and a second strand, and wherein a first strand of the PCR amplification reaction product is a copy of the polynucleotide template. Next, the PCR reaction product (which comprises a copy of the polynucleotide template) may be used as a template in a non-thermocycling amplification reaction as provided in PCT/US14/56151, in order to generate a non-thermocycling reaction product as described in PCT/US14/56151. Such non-thermocycling reaction products may include concatemers. In embodiments of this method involving a PCR amplification reaction followed by a non-thermocycling amplification reaction, only the non-thermocycling reaction products are detected (not the PCR reaction products). In embodiments, the non-thermocycling reaction products are detected in real-time as they are formed. In embodiments, a method of PCT/US14/56151 may involve a first primer and a second primer. In embodiments, the first primer of a method of PCT/US14/56151 contains a first region and a second region, wherein the first region comprises a 5' end of the primer, the second region comprises a 3' end of the primer, and the second region is complementary to a least a portion of a first strand of a double-stranded nucleic acid template (i.e. a double-stranded nucleic acid molecule, such as a PCR amplification reaction product). In embodiments, the second primer of a method of PCT/US14/56151 contains a first region and a second region, wherein the first region comprises a 5' end of the primer and is complementary to the first region of the first primer, the second region comprises a 3' end of the primer, and wherein the second region is complementary to a least a portion of a second strand of the double-stranded nucleic acid template. In embodiments, the second region of a first primer of a method of PCT/US14/56151 may anneal to a first strand of a PCR amplification reaction product in methods herein in the same way as a first PCR amplification reaction primer anneals to a polynucleotide template strand in PCR amplification reactions provided herein, and the second region of a second primer of a method of PCT/US14/56151 may anneal to a second strand of a PCR amplification reaction product as provided in methods herein in the same way as a second PCR amplification reaction primer anneals to a polynucleotide which is complementary to the polynucleotide template in PCR amplification reaction methods provided herein.

A "primer" as used herein may refer to a polynucleotide which is i) capable of hybridizing to an original nucleic acid strand and ii) acting as a point of initiation for the synthesis of a new nucleic acid strand, wherein the new nucleic acid strand is an extension product of the primer and is complementary to the original strand. A primer may have a free —OH group at its 3' terminus, which may serve as the origin of synthesis for the extension product.

A primer may contain standard nucleotides [e.g. standard DNA deoxyribonucleotides (deoxyadenosine monophosphate, deoxyguanosine monophosphate, thymidine monophosphate, deoxycytidine monophosphate) or standard RNA ribonucleotides (adenosine monophosphate, guanosine monophosphate, uridine monophosphate, cytidine monophosphate)], alternative nucleotides (e.g. inosine), modified nucleotides, nucleotide analogs, or a combination thereof. For example, an oligonucleotide primer may include peptide nucleic acids, morpholinos (e.g. phosphorodiamidate morpholino oligos), locked nucleic acids [see, for example, Kaur, H, et. al, Biochemistry 45 (23), 7347-55 (2006)], glycol nucleic acids, or threose nucleic acids. A primer may have a backbone, including, for example, phosphodiester linkages, phosphorothioate linkages (a non-bridging O is replaced with sulfur), or peptide linkages (as part of a peptide nucleic acid). Alternative nucleotides, modified nucleotides, and nucleotide analogs may be referred to collectively herein as "non-standard nucleotides."

The presence of a non-standard nucleotide in a primer may affect various properties of the primer. In some embodiments, inclusion of a non-standard nucleotide in a primer may increase or decrease the thermodynamic stability of a primer to a complementary sequence thereof. For example, a primer having increased thermodynamic stability may contain a locked nucleic acid. A primer having decreased thermodynamic stability may contain, for example, inosine (described by Auer et al., Nucl. Acids Res. 24; 5021-5025 (1996)) or a negatively charged chemical group, such as a carboxylic acid.

A first primer or a second primer provided herein may be of any length. The first primer and second primer may contain the same number of nucleotides, or a different number of nucleotides. In some embodiments, a first or second primer may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, a first or second primer may be no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, a first or second primer may have a length selected from a range having a minimum value of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, or 1000 nucleotides in length, and a maximum value of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length.

The presence of amplified nucleic acids can be assayed, for example, by detection of reaction products (amplified nucleic acids or reaction by-products) or by detection of probes associated with the reaction progress.

In some embodiments, reaction products may be identified by staining the products with a dye. In some embodiments, a dye may have greater fluorescence when bound to a nucleic acid than when not bound to a nucleic acid. In embodiments, a dye may intercalate with a double-stranded nucleic acid or it may bind to an external region of a nucleic acid. Nucleic acid dyes that may be used with methods and compositions provided herein include, for example, cyanine dyes, PicoGreen®, OliGreen®, RiboGreen®, SYBR® dyes, SYBR® Gold, SYBR® Green I, SYBR® Green II, ethidium bromide, dihydroethidium, BlueView™, TOTO® dyes, TO-PRO® dyes, POPO® dyes, YOYO® dyes, BOBO® dyes, JOJO® dyes, LOLO® dyes, SYTOX® dyes, SYTO® dyes, propidium iodide, hexidium iodide, methylene blue, DAPI, acridine orange, quinacrine, acridine dimers, 9-amino-6-chloro-2-methoxyacridine, bisbenzimide dyes, Hoechst dyes, 7-aminoactinomycin D, actinomycin D, hydroxystilbamidine, pyronin Y, Diamond™ dye, GelRed™, GelGreen™ and LDS 751.

In some embodiments, reaction products may be identified by analysis of turbidity of amplification reactions. For example, in embodiments, increased turbidity may be correlated with formation of reaction products and reaction by-products (e.g. pyrophosphate complexed with magnesium).

In some embodiments, reaction products may be identified by separating a reaction performed according to a method herein by gel electrophoresis, followed by staining of the gel with a dye for nucleic acids. The dye may be any nucleic acid dye disclosed herein or otherwise known in the art.

In some embodiments, any method or composition known in the art for the detection of nucleic acids or for the generation of nucleic acids may be used with methods and compositions provided herein.

In some embodiments, a reaction performed according to a method provided herein may be monitored in an apparatus containing a light source and an optical sensor. In some situations, the reaction may be positioned in the path of light from the light source, and light absorbed by the sample (e.g. in the case of a turbid reaction), scattered by the sample (e.g. in the case of a turbid reaction), or emitted by the sample (e.g. in the case of a reaction containing a fluorescent molecule) may be measured. In some embodiments, a method provided herein may be performed or monitored in a device or module therein as disclosed in U.S. patent application Ser. No. 13/769,779, filed Feb. 18, 2013, which is herein incorporated by reference in its entirety.

Using methods provided herein, specific amplification products of a nucleic acid template of interest may be identified within, for example, 30 seconds, 1 minute, 3 minutes, 5 minutes, 10 minutes, 15 minutes, 20 minutes, 30 minutes, 45 minutes, 60 minutes, 90 minutes, 120 minutes, 180 minutes, or 240 minutes of initiation of an amplification reaction. In other examples, using methods provided herein, amplification reactions which are positive for a nucleic acid template of interest may be identified when as few as 10, 50, 100, 500, 1000, 5000, 10,000, 50,000, 100,000, 500,000, or 1,000,000 copies of the template are generated. In other examples, using methods provided herein, the presence of a nucleic acid template of interest in a sample containing as few as 1, 2, 3, 4, 5, 10, 15, 20, 25, 30, 40, 50, 100, 200, 500, 1000, 5000, or 10,000 copies of the template of interest at the start of the method may be identified.

In embodiments, methods provided herein may be used to assay a sample for a target nucleic acid of interest. In certain embodiments, the presence or quantity of a target nucleic acid of interest in a sample may be determined by a method involving determining an inflection time for nucleic acid amplification in a reaction. An inflection time/inflection point is a time or a point where an amplification reaction is determined as being positive for a nucleic acid template. An inflection time/point may be identified by one or more indicators, such as for example, the time post-initiation of a reaction when a selected quantity of nucleic acid has been generated in the reaction, the time when the rate of amplification in a reaction changes from a baseline phase to an exponential phase, or the time when the rate of amplification in a reaction changes from an exponential phase to a plateau phase, etc. In embodiments, an inflection time/point may be identified based on a change in fluorescence or absorbance of a reaction, or upon the fluorescence or absorbance of a reaction reaching a selected value. In certain embodiments, the presence or quantity of a target nucleic acid of interest in a sample may be determined by a method involving comparison of an inflection time for nucleic acid amplification of a reaction of which has an unknown amount of target nucleic acid of interest versus one or both of: i) a reaction which is known to lack the target nucleic acid of interest (i.e. a negative control) or ii) a reaction which is known to contain the target nucleic acid of interest (i.e. a positive control). In embodiments, both a reaction which contains the target nucleic acid of interest and a reaction which does not contain the target nucleic acid may be measured for a selected inflection time. In embodiments, the presence of a target nucleic acid of interest in a sample may be determined based on a method which involves evaluation of the difference in time between inflection of a reaction containing a sample which may or may not contain a target nucleic acid of interest, and a time of inflection of one or more reactions with known target nucleic acid of interest status (e.g. which are known to contain or not contain the target nucleic acid of interest). For example, a sample may be identified as containing a target nucleic acid of interest if the inflection time of the reaction according to a method provided herein is at least 3, 5, 10, 15, 20, 30, 40, 50, 60, 90, 120, or 180 minutes earlier than a corresponding reaction which is known to not contain the target nucleic acid of interest. In another example, a sample may be identified as containing a target nucleic acid of interest if the inflection time of the reaction according to a method provided herein is no more than 3, 5, 10, 15, 20, 30, 40, 50, 60, 90, 120, or 180 minutes later than a corresponding reaction which is known to contain the target nucleic acid of interest.

Methods provided herein may be performed for any length of time. Typically, the method will be performed for a length of time sufficient to monitor, for example, the rate of nucleic acid replication, the occurrence of polymerase activity, or the accumulation of amplification product. In some embodiments, a method provided herein may be performed for a total of less than 10 seconds, 30 seconds, 1 minute, 5 minutes, 10 minutes, 20 minutes, 30 minutes, 45 minutes, 1 hour, 2 hours, 3 hours, 4 hours, 6 hours, 8 hours, 12 hours, 16 hours, or 24 hours, by which time the rate of nucleic acid replication, the occurrence of polymerase activity, or the accumulation of amplification product is measured.

Methods provided herein may be terminated in various ways. In one embodiment, steps of a method may end upon the reduction in concentration or complete consumption of one or more reagents involved in one or more steps of the method (e.g. dNTPs). In another embodiment, steps of a method may end upon inactivation of one or more enzymes involved in one or more steps of the method (e.g. polymerases). Enzymes may be inactivated by various ways. For example, enzymes may gradually lose enzymatic activity over time due to random events that affect the structure of the enzyme, or enzymes may be exposed to a condition to accelerate the inactivation of the enzyme activity (e.g. high heat, extreme pH, etc.).

In methods provided herein, generation of nucleic acid concatemers also amplifies the number of copies of the nucleic acid template/particular nucleic acid in the concatemer. Accordingly, references herein to methods and compositions for the generation of concatemers also apply to the amplification of nucleic acids.

As used herein, a "polynucleotide" refers to a polymeric chain containing two or more nucleotides. "Polynucleotides" includes primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3' terminus) of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide.

The term "downstream" as used herein in the context of a polynucleotide containing a 5' terminal nucleotide and a 3' terminal nucleotide refers to a position in the polynucleotide which is closer to the 3' terminal nucleotide than a reference position in the polynucleotide. For example, in a primer having the sequence: 5' ATAAGC 3', the "G" is downstream from the "T" and all of the "A"s.

The term "upstream" as used herein in the context of a polynucleotide containing a 5' terminal nucleotide and a 3' terminal nucleotide, refers to a position in the polynucleotide which is closer to the 5' terminal nucleotide than a reference position in the polynucleotide. For example, in a primer having the sequence: 5' ATAAGC 3', the "T" is upstream from the "G", the "C", and the two "A"s closest to the "G".

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded.

As used herein, a "concatemer" refers to a nucleic acid molecule which contains within it two or more copies of a particular nucleic acid, wherein the copies are linked in series. Within the concatemer, the copies of the particular nucleic acid may be linked directly to each other, or they may be indirectly linked (e.g. there may be nucleotides between the copies of the particular nucleic acid). In an example, the particular nucleic acid may be that of a double-stranded nucleic acid template, such that a concatemer may contain two or more copies of the double-stranded nucleic acid template. In another example, the particular nucleic acid may be that of a polynucleotide template, such that a concatemer may contain two or more copies of the polynucleotide template.

As used herein, a "target" nucleic acid or molecule refers to a nucleic acid of interest. A target nucleic acid/molecule may be of any type, including single-stranded or double stranded DNA or RNA (e.g. mRNA).

As used herein, "complementary" sequences refer to two nucleotide sequences which, when aligned anti-parallel to each other, contain multiple individual nucleotide bases which can pair with each other according to standard base-pairing rules (e.g. A-T, G-C, or A-U), such that molecules containing the sequences can specifically anneal to each other. It is not necessary for every nucleotide base in two sequences to be capable of pairing with each other for the sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences can pair with each other when the sequences are optimally aligned for complementation. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer can pair with nucleotide bases in the longer polynucleotide when the primer is aligned anti-parallel to a particular region of the longer polynucleotide. Additionally, "complementary" sequences may contain one or more nucleotide analogs or nucleobase analogs. As used herein, "perfectly complementary" or "perfect complementation" or the like refers two sequences which are 100% complementary to each other (i.e. where there are no mis-matches between the nucleotides of the sequences when the sequences are paired for maximum complementation). Also, references herein to a first polynucleotide that "has a nucleotide sequence which is complementary" to a second polynucleotide and the like has the same meaning as saying that the first polynucleotide "is complementary" to the second polynucleotide.

As used herein, the term "isolated" as applied to proteins, nucleic acids, or other biomolecules refers to a molecule that has been purified or separated from a component of its naturally-occurring environment (e.g. a protein purified from a cell in which it was naturally produced). An "isolated" molecule may be in contact with other molecules (for example, as part of a reaction mixture). As used herein, "isolated" molecules also include recombinantly-produced proteins or nucleic acids which have an amino acid or nucleotide sequence which occurs naturally. "Isolated" nucleic acids include polypeptide-encoding nucleic acid molecules contained in cells that ordinarily express the polypeptide where, for example, the nucleic acid molecule is at a chromosomal location different from that of natural cells. In some embodiments, "isolated" polypeptides are purified to at least 50%, 60%, 70%, 80%, 90%, 95%, 98%, or 100% homogeneity as evidenced by SDS-PAGE of the polypeptides followed by Coomassie blue, silver, or other protein staining method.

As used herein, a nucleic acid molecule which is described as containing the "sequence" of a template or other nucleic acid may also be considered to contain the template or other nucleic acid itself (e.g. a molecule which is described as containing the sequence of a template may also be described as containing the template), unless the context clearly dictates otherwise.

As used herein, when a first polynucleotide is described as "annealed", "annealing" or the like to a second polynucleotide, the entirety of the first polynucleotide or any portion thereof may anneal to the second polynucleotide, and vice versa.

As used herein, references to "generating a copy of a template" and the like includes both i) generation of an exact copy of a template (e.g. generating a DNA copy of a DNA template) and ii) generation of a DNA version of an RNA template. For instance, a template may be a single-strand RNA molecule (such as from a single-stranded RNA virus). This template may be copied by reverse transcription PCR, which results in many copies of the DNA version of the RNA template.

As used herein, a reference to "treating" a given object to a condition or other object or the like refers to directly or indirectly exposing the given object to the recited condition or other object. Thus, while a "treating" step may involve a distinct related action (e.g. adding an enzyme to a vessel, shaking a vessel, etc.), not every "treating" step requires a distinct related action. For example, a reaction involving one or more reagents can be set up in a vessel, and once the reaction has been initiated, multiple events or steps may occur in the vessel without further human or mechanical intervention with the contents of the vessel. One or more of these multiple events or steps in the vessel may be described as "treating" an object in the vessel, even if no separate intervention with the contents of the vessel occurs after the initiation of the reaction.

In some embodiments, a nucleic acid template may be single stranded or double-stranded. A single strand of a nucleic acid template may be referred to herein as a "polynucleotide template". A "polynucleotide template" as referred to herein is not precluded from binding to a complementary sequence thereof. In other words, a "polynucleotide template" may be, for example, the entirety of a single-stranded nucleic acid template, or it may be one strand of a double-stranded nucleic acid template. A nucleic acid template may be contained in a primary nucleic acid molecule.

In some embodiments, a nucleic acid template may constitute the entirety of a primary nucleic acid molecule. In other embodiments, a nucleic acid template may be contained in a primary nucleic acid which contains one or more nucleotides which are not part of the nucleic acid template (e.g. the nucleic acid template may be of a shorter length than the primary nucleic acid which contains the nucleic acid template).

With methods provided herein pathogens or genes may be positively identified at concentrations as low as, for example, less than 1000, 500, 100, 50, 10, 5, 2, or 1 copy per microliter in a sample or a reaction mixture. In embodiments, methods provided herein may specifically amplify nucleic acid from one type of pathogen or gene and not amplify nucleic acid from a related pathogen or gene. For example, assays provided herein to amplify Influenza A matrix protein gene may amplify this gene from multiple different strains of Influenza A, but not amplify genetic material from Influenza B.

In embodiments, methods provided herein may be successfully performed in the presence of one or more potentially interfering substances. Examples of potentially interfering substances include BSA, glucose, bilirubin, nitrites, beta-hCG, acetone, low pH conditions, high pH conditions, acetaminophen, aspirin, progestin, ethinyl estradiol, urine preservatives, seminal fluid, personal lubricants, contraceptive jellies, spermicides, feminine powders, hemorrhoid creams, miconzole, human genomic DNA, lotions, universal transport media (viral), amies transport media (bacteria), blood, mucin, acyclovir, cold sore treatments, urine, feces, hemoglobin, triglycerides, EDTA, heparin, cholesterol, gamma-globulin, ampicillin, nicotine, cotinine, nasal sprays, nasal drops, or any combination thereof. In embodiments, methods provided herein may be performed in the presence of a potentially interfering substance which is at a concentration of up to at least as great as provided in U.S. Provisional Patent Application No. 62/001,050, filed May 20, 2014, which is hereby incorporated by reference for all purposes. In embodiments, methods provided herein may be performed in the presence of a potentially interfering substance which is at a concentration of up to at least 10%, 25%, 50%, or 100% greater than provided in U.S. Provisional Patent Application No. 62/001,050.

The assays and methods disclosed herein may be performed on a device, or on a system, for processing a sample. The assays and methods disclosed herein can be readily incorporated into and used in a device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be a sample processing device. A device may be a sample processing device. A sample processing device may be configured to facilitate collection of a sample, prepare a sample for a clinical test, or perform a method with one or more reagents, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to be placed in or on a subject. A sample processing device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. A cartridge may contain reagents disclosed herein for the performing a method disclosed herein. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have a portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assays on a sample, and to obtain data from the sample. A sample processing device may perform methods provided herein, as well as additional assays. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example, one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, less than about 5 µL, less than about 1 µL, less than about 0.5 µL, less than about 0.1 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. In some embodiments, a sample processing device may be configured to perform a method provided herein and one, two, or more additional assays. In embodiments, a sample processing device may be configured to perform a plurality of assays on a single sample. In embodiments, a sample processing device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, less than about 5 µL, less than about 1 µL, less than about 0.5 µL, less than about 0.1 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte (e.g. a target nucleic acid) or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing steps may be performed, with or without the sample. Examples of steps, tests, or assays that may be prepared or run by the device may include, but are not limited to immunoassay, nucleic acid assay (e.g. methods provided herein), receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, a sample processing device may be configured to transmit data obtained from a sample. In embodiments, a sample processing device may be configured to communicate over a network. A sample processing device may include a communication module that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by a sample processing device, or analysis of such data, or reports, may be provided to a database, an electronic medical records system, to a laboratory information system, to a laboratory automation system, or other system or software.

Description and disclosure of examples of reagents, assays, methods, kits, devices, and systems which may use, or be used with, methods, compositions, or other reagents disclosed herein may be found, for example, in U.S. Pat. No. 8,088,593; U.S. Pat. No. 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; International Application No. PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, International Application No. PCT/US14/30034, filed Mar. 15, 2014, and U.S. patent application Ser. No. 14/214,850, filed Mar. 15, 2014, the disclosures of which patents and patent applications are all hereby incorporated by reference in their entireties.

This application claims the benefit of, and priority to U.S. Provisional Patent Application No. 62/051,912, filed Sep. 17, 2014; U.S. Provisional Patent Application No. 62/051,945, filed Sep. 17, 2014; U.S. Provisional Patent Application No. 62/068,603, filed Oct. 24, 2014; U.S. Provisional Patent Application No. 62/068,605, filed Oct. 24, 2014; U.S. Provisional Patent Application No. 62/151,358, filed Apr. 22, 2015; U.S. Non-Provisional patent application Ser. No. 14/214,850, filed Mar. 15, 2014; International Patent Application No. PCT/US14/30034, filed Mar. 15, 2014; and International Patent Application No. PCT/US14/56151, filed Sep. 17, 2014, the disclosure of each of which is also hereby incorporated by reference in its entirety for all purposes.

The disclosures of U.S. Provisional Patent Application No. 61/908,027, filed Nov. 22, 2013; U.S. Provisional Patent Application No. 62/001,050, filed May 20, 2014; and U.S. Provisional Patent Application No. 61/800,606, filed Mar. 15, 2013 are also hereby incorporated by reference in their entirety for all purposes.

Methods and Compositions as Provided in PCT/US14/56151

In embodiments, methods and compositions provided herein may include methods or compositions as provided in PCT/US14/56151, filed Sep. 17, 2014, which is hereby incorporated by reference in its entirety for all purposes. Methods provided in PCT/US14/56151 may be performed without thermocycling. Exemplary methods and compositions as provided in PCT/US14/56151 are provided below. The descriptions below are also applicable to methods and compositions as provided herein, as appropriate for the context.

In some embodiments, provided herein is a method for generating a concatemer comprising two or more copies of a double-stranded nucleic acid template, the method comprising: (A) treating a primary double-stranded nucleic acid comprising the double-stranded nucleic acid template with a first copy of a first primer and a polymerase under conditions such that an extension product of the first copy of the first primer is synthesized which is annealed to a first strand of the double-stranded nucleic acid template, wherein the first primer comprises a 5' terminal nucleotide, a 3' terminal nucleotide, and two regions: (i) a tail region comprising: (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, and the template-binding region of the first copy of the first primer anneals to the first strand of the double-stranded nucleic acid template, (B) treating the extension product of the first copy of the first primer of step (A) with a second primer and a polymerase under conditions such that an extension product of the second primer is synthesized which is annealed to the extension product of the first copy of the first primer of step (A), wherein the second primer comprises a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, the tail region of the second primer contains a nucleotide sequence which is complementary to the nucleotide sequence of the tail region of the first primer, if the sequences are aligned such that the 5' terminal nucleotide of the second primer is aligned with the innermost nucleotide of the tail region of the first primer and the 5' terminal nucleotide of the first primer is aligned with the innermost nucleotide of the tail region of the second primer, the template-binding region of the second primer anneals to the extension product of the first copy of the first primer of step (A), and the extension product of the second primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the second primer read in the 5' to 3' direction, and the final nucleotide of the 3' terminal region is the 3' terminal nucleotide of the extension product of the second primer, (C) treating the extension product of the second primer of step (B) with a second copy of the first primer and a polymerase under conditions such that an extension product of the second copy of the first primer is synthesized which is annealed to the extension product of the second primer of step (B), to produce a first copy of a secondary nucleic acid comprising the extension product of the second primer of step (B) and the extension product of the second copy of the first primer, wherein the extension product of the second copy of the first primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the first primer read in the 5' to 3' direction, and the final nucleotide of the 3' terminal region is the 3' terminal nucleotide of the extension product of the second primer, (D) repeating at least step (C) one or more addition times to generate at least a second copy of the secondary nucleic acid of step (C), (E) treating the first copy of the secondary nucleic acid of step (C) and the second copy of the secondary nucleic acid of step (D) under conditions such that the 3' terminal region of the extension product of the second copy of the first primer of the first copy of the secondary nucleic acid anneals to the 3' terminal region of the extension product of the second primer of the second copy of the secondary nucleic acid, to produce a cross-over structure comprising the extension product of the second copy of the first primer of the first copy of the secondary nucleic acid and the extension product of the second primer of the second copy of the secondary nucleic acid, (F) treating the cross-over structure of step (E) with a polymerase under conditions such that an extension product of the extension product of the second copy of the first primer of the first copy of the secondary nucleic acid is synthesized and an extension product of the extension product of the second primer of the second copy of the secondary nucleic acid is synthesized, to produce a concatemer comprising two copies of the double-stranded nucleic acid template of step (A), wherein the concatemer comprises the extension product of the extension product of the second copy of the first primer of the first copy of the secondary nucleic acid and the extension product of the extension product of the second primer of the second copy of the secondary nucleic acid.

In some embodiments, provided herein is a method for generating a concatemer comprising two or more copies of a polynucleotide template or an analogous sequence thereof, the method comprising, (A) treating a primary nucleic acid comprising the polynucleotide template with a first copy of a first primer and a polymerase under conditions such that an extension product of the first copy of the first primer is synthesized which is annealed to the polynucleotide template, wherein the first primer comprises a 5' terminal nucleotide, a 3' terminal nucleotide, and two regions: (i) a tail region comprising (a) the 5' terminal nucleotide of the primer, (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, and the template-binding region of the first copy of the first primer anneals to the polynucleotide template, (B) treating the extension product of the first copy of the first primer of step (A) with a second primer and a polymerase under conditions such that an extension product of the second primer is synthesized which is annealed to the extension product of the first copy of the first primer of step (A), wherein the second primer comprises a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, the tail region of the second primer contains a nucleotide sequence which is complementary to the nucleotide sequence of the tail region of the first primer, if the sequences are aligned such that the 5' terminal nucleotide of the second primer is aligned with the innermost nucleotide of the tail region of the first primer and the 5' terminal nucleotide of the first primer is aligned with the innermost nucleotide of the tail region of the second primer, the template-binding region of the second primer anneals to the extension product of the first copy of the first primer of step (A), and the extension product of the second primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the second primer read in the 5' to 3' direction, and the final nucleotide of the 3' terminal region is the 3' terminal nucleotide of the extension product of the second primer, (C) treating the extension product of the second primer of step (B) with a second copy of the first primer and a polymerase under conditions such that an extension product of the second copy of the first primer is synthesized which is annealed to the extension product of the second primer of step (B), to produce a first copy of a secondary nucleic acid comprising the extension product of the second primer of step (B) and the extension product of the second copy of the first primer, wherein the extension product of the second copy of the first primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the first primer read in the 5' to 3' direction, and the final nucleotide of the 3' terminal region is the 3' terminal nucleotide of the extension product of the second primer, (D) repeating at least step (C) one or more additional times to generate at least a second copy of the secondary nucleic acid comprising the extension product of the second primer of step (B) and the extension product of the second copy of the first primer of step (C), (E) treating the first copy of the secondary nucleic acid of step (C) and the second copy of the secondary nucleic acid of step (D) under conditions such that the 3' terminal region of the extension product of the second copy of the first primer of the first copy of the secondary nucleic acid anneals to the 3' terminal region of the extension product of the second primer of the second copy of the secondary nucleic acid, to produce a cross-over structure comprising the extension product of the second copy of the first primer of the first copy of the secondary nucleic acid and the extension product of the second primer of the second copy of the secondary nucleic acid, (F) treating the cross-over structure of step (E) with a polymerase under conditions such that an extension product of the extension product of the second copy of the first primer of the first copy of the secondary nucleic acid is synthesized and an extension product of the extension product of the second primer of the second copy of the secondary nucleic acid is synthesized, to produce a concatemer comprising two copies of the polynucleotide template of step (A), wherein the concatemer comprises the extension product of the extension product of the second copy of the first primer of the first copy of the secondary nucleic acid and the extension product of the extension product of the second primer of the second copy of the secondary nucleic acid. In some embodiments, the nucleic acid polymerase of step (A) is a DNA polymerase. In some embodiments, the nucleic acid polymerase of step (A) is a reverse transcriptase.

In some embodiments, provided herein is a method for generating a concatemer comprising two or more copies of a double-stranded nucleic acid template, the method comprising, (A) preparing a reaction mixture comprising: (i) a primary nucleic acid comprising the double-stranded nucleic acid template (ii) an isolated nucleic acid polymerase, (iii) a first primer comprising a 5' terminal nucleotide, a 3' terminal nucleotide, and two regions: (a) a tail region comprising (1) the 5' terminal nucleotide of the primer (2) an innermost nucleotide, wherein the innermost nucleotide is downstream from the 5' terminal nucleotide (3) a middle section between the 5' terminal nucleotide and the innermost nucleotide, comprising one or more nucleotides, and (b) a template-binding region comprising (1) the 3' terminal nucleotide of the primer (2) an innermost nucleotide, wherein the innermost nucleotide is upstream from the 3' terminal nucleotide (3) a middle section between the 3' terminal nucleotide and the innermost nucleotide, comprising one or more nucleotides, wherein the template-binding region is complementary to a first strand of the nucleic acid template, (iv) a second primer comprising a 5' terminal nucleotide, a 3' terminal nucleotide, and two regions: (a) a tail region comprising (1) the 5' terminal nucleotide of the primer (2) an innermost nucleotide, wherein the innermost nucleotide is downstream from the 5' terminal nucleotide (3) a middle section between the 5' terminal nucleotide and the innermost nucleotide, comprising one or more nucleotides, and (b) a template-binding region comprising (1) the 3' terminal nucleotide of the primer (2) an innermost nucleotide, wherein the innermost nucleotide is upstream from the 3' terminal nucleotide (3) a middle section between the 3' terminal nucleotide and the innermost nucleotide, comprising one or more nucleotides, and wherein the template-binding region is complementary to a second strand of the nucleic acid template, and wherein the tail region of the second primer contains a nucleotide sequence which is complementary to the nucleotide sequence of the tail region of the first primer, if the sequences are aligned such that the 5' terminal nucleotide of the second primer is aligned with the innermost nucleotide of the tail region of the first primer and the 5' terminal nucleotide of the first primer is aligned with the innermost nucleotide of the tail region of the second primer, and (B) incubating the reaction mixture for at least 3 minutes without thermocycling.

In some embodiments, provided herein is a method for generating a concatemer comprising two or more copies of a polynucleotide template, the method comprising, (A) preparing a reaction mixture comprising: (i) a nucleic acid comprising the polynucleotide template (ii) an isolated nucleic acid polymerase, (iii) a first primer comprising a 5' terminal nucleotide, a 3' terminal nucleotide, and two regions: (a) a tail region comprising (1) the 5' terminal nucleotide of the primer (2) an innermost nucleotide, wherein the innermost nucleotide is downstream from the 5' terminal nucleotide (3) a middle section between the 5' terminal nucleotide and the innermost nucleotide, comprising one or more nucleotides, and (b) a template-binding region comprising (1) the 3' terminal nucleotide of the primer (2) an innermost nucleotide, wherein the innermost nucleotide is upstream from the 3' terminal nucleotide (3) a middle section between the 3' terminal nucleotide and the innermost nucleotide, comprising one or more nucleotides, and wherein the template-binding region is complementary to the polynucleotide template, (iv) a second primer comprising a 5' terminal nucleotide, a 3' terminal nucleotide, and two regions: (a) a tail region comprising (1) the 5' terminal nucleotide of the primer (2) an innermost nucleotide, wherein the innermost nucleotide is downstream from the 5' terminal nucleotide (3) a middle section between the 5' terminal nucleotide and the innermost nucleotide, comprising one or more nucleotides, and (b) a template-binding region comprising (1) the 3' terminal nucleotide of the primer (2) an innermost nucleotide, wherein the innermost nucleotide is upstream from the 3' terminal nucleotide (3) a middle section between the 3' terminal nucleotide and the innermost nucleotide, comprising one or more nucleotides, and wherein the template-binding region is complementary to a nucleotide sequence complementary to the polynucleotide template, and wherein the tail region of the second primer contains a nucleotide sequence which is complementary to the nucleotide sequence of the tail region of the first primer, if the sequences of the primers are aligned such that the 5' terminal nucleotide of the second primer is aligned with the innermost nucleotide of the tail region of the first primer and the 5' terminal nucleotide of the first primer is aligned with the innermost nucleotide of the tail region of the second primer, and (B) incubating the reaction mixture at a temperature of no greater than 80 C for at least 3 minutes.

In some embodiments, provided herein is a method for generating a concatemer comprising two or more copies of a double-stranded nucleic acid template, the method comprising incubating together a first copy and a second copy of a double-stranded nucleic acid molecule comprising the double-stranded nucleic acid template and a polymerase, wherein the double-stranded nucleic acid molecule comprises a first strand and a second strand, each containing a plurality of nucleotides, the first strand comprises a 5' terminal nucleotide and a 3' terminal nucleotide and contains the general format of regions in the 5' to 3' direction: A1-B-A2, the second strand comprises a 5' terminal nucleotide and a 3' terminal nucleotide and contains the general format of regions in the 5' to 3' direction: C1-D-C2, region B comprises the nucleotide sequence a first strand of the double-stranded nucleic acid template, region D comprises the nucleotide sequence of a second strand of the double-stranded nucleic acid template, in the double-stranded nucleic acid molecule, region A1 is annealed to C2, B is annealed to D, and A2 is annealed to C1, a cross-over structure comprising the first strand of the first copy of the double-stranded nucleic acid molecule and the second strand of the second copy of the double-stranded nucleic acid molecule is generated, wherein the A2 region of the first strand is annealed to the C2 region of the second strand, an extension product of the first strand of the cross-over structure is synthesized and an extension product of the second strand of the cross-over structure is synthesized, to produce a concatemer comprising the extension product of the first strand of the cross-over structure annealed to the extension product of the second strand of the cross-over structure, wherein the concatemer contains two copies of the double-stranded nucleic acid template.

In embodiments, provided herein is a method of copying a polynucleotide template, the method comprising: incubating the polynucleotide template in a reaction mixture comprising multiple copies of a first primer and multiple copies of a second primer, wherein: the first primer comprises a first region and a second region, wherein the second region of the first primer comprises a nucleotide sequence which is complementary to a first portion of the polynucleotide template; the second primer comprises a first region and a second region, wherein the second region of the second primer comprises a nucleotide sequence which is complementary to a partner nucleotide sequence, wherein the partner nucleotide sequence is complementary to a second portion of the polynucleotide template; and upon incubation of the polynucleotide template with the multiple copies of the first primer and the multiple copies of the second primer, at least one concatemer strand is formed, wherein the concatemer strand comprises a 5' end and a 3' end, and comprises a nucleotide sequence having the general structure in the 5' to 3' direction of: C'-T-C'-T-X-C', wherein: C' represents the nucleotide sequence of the first region of the second primer, T represents the nucleotide sequence of the polynucleotide template or an analogous sequence thereof, and X represents any number and sequence of nucleotides.

In some embodiments, in a method provided herein involving the formation of a concatemer strand which comprises a nucleotide sequence having the general structure in the 5' to 3' direction of: C'-T-C'-T-X-C', the concatemer strand is a first concatemer strand, and a second concatemer strand is also formed, wherein the second concatemer strand comprises a 5' end and a 3' end, and comprises a nucleotide sequence having the general structure in the 5' to 3' direction of: C-X'-T'-C-T'-C, wherein: C represents the nucleotide sequence of the first region of the first primer, T' represents a nucleotide sequence which is complementary to the polynucleotide template, and X' represents a nucleotide sequence which is complementary to the nucleotide sequence of X.

In embodiments, provided herein is method of assaying for a target polynucleotide template in a biological sample, the method comprising: A) incubating the biological sample or portion thereof in a reaction mixture comprising multiple copies of a first primer and multiple copies of a second primer, wherein: the first primer comprises a first region and a second region, wherein the second region of the first primer comprises a nucleotide sequence which is complementary to a first portion of the polynucleotide template; the second primer comprises a first region and a second region, wherein the second region of the second primer comprises a nucleotide sequence which is complementary to a partner nucleotide sequence, wherein the partner nucleotide sequence is complementary to a second portion of the polynucleotide template; and upon incubation of the polynucleotide template with the multiple copies of the first primer and the multiple copies of the second primer, at least one concatemer strand is formed, wherein the concatemer strand comprises a 5' end and a 3' end, and comprises a nucleotide sequence having the general structure in the 5' to 3' direction of: C'-T-C'-T-X-C', wherein: C' represents the nucleotide sequence of the first region of the second primer, T represents the nucleotide sequence of the polynucleotide template or an analogous sequence thereof, and X represents any number and sequence of nucleotides; and B) measuring an amount of amplified nucleic acid in the reaction mixture of A) at one or more points after the initiation of the incubating step of A). In embodiments, the measuring an amount of amplified nucleic acid in the reaction mixture may comprise determining a level of fluorescence in the reaction mixture. In embodiments, the method may further comprise determining an inflection time of nucleic acid amplification in the reaction mixture.

In embodiments, in a method, reaction mixture, vessel, or kit provided herein involving a concatemer strand which comprises a nucleotide sequence having the general structure in the 5' to 3' direction of: C'-T-C'-T-X-C', X may contain a sequence having the general structure in the 5' to 3' direction of $[(C'-T)_N]$ wherein C' represents the nucleotide sequence of the first region of the second primer, T represents the nucleotide sequence of the polynucleotide template or an analogous sequence thereof, and N is any integer between 0 and 2000. In embodiments, N may be any integer between 0 and 10, 0 and 100, 0 and 1000, 0 and 5000, 0 and 10,000 1 and 10, 1 and 100, 1 and 1000, 1 and 2000, 1 and 5000, or 1 and 10,000.

In embodiments, in a method, reaction mixture, vessel, or kit provided herein involving a concatemer strand which comprises a nucleotide sequence having the general structure in the 5' to 3' direction of: C'-T-C'-T-X-C', X may contain no more than 0, 1, 2, 3, 4, 5, 6, 7, 8, 9, 10, 15, 20, 25, 50, 100, 500, 1000, 10,000, 50,000, 100,000, or 500,000 nucleotides. In embodiments, in a method, vessel, or kit provided herein involving a concatemer strand which comprises a nucleotide sequence having the general structure in the 5' to 3' direction of: C'-T-C'-T-X-C', X may contain at least 1, 2, 3, 4, 5, 6, 7, 8, 9, 10, 15, 20, 25, 50, 100, 500, 1000, 10,000, 50,000, 100,000, or 500,000 nucleotides. In embodiments, in a method, vessel, or kit provided herein involving a concatemer strand which comprises a nucleotide sequence having the general structure in the 5' to 3' direction of: C'-T-C'-T-X-C', X may contain at least 1, 2, 3, 4, 5, 6, 7, 8, 9, 10, 15, 20, 25, 50, 100, 500, 1000, 10,000, 50,000, 100,000, nucleotides, and no more than 2, 3, 4, 5, 6, 7, 8, 9, 10, 15, 20, 25, 50, 100, 500, 1000, 10,000, 50,000, 100,000, or 500,000 nucleotides.

In embodiments, in a method, reaction mixture, vessel, or kit provided herein involving a concatemer strand which comprises a nucleotide sequence having the general structure in the 5' to 3' direction of: C'-T-C'-T-X-C', between at least one C' and T, one or more extra nucleotides are present which are not part of the C' or T sequence. The one or more extra nucleotides may be, for example, between 1 and 10, 1 and 20, 1 and 100, or 1 and 1000 nucleotides.

In embodiments, in a method, reaction mixture, vessel, or kit provided herein involving a concatemer strand which comprises a nucleotide sequence having the general structure in the 5' to 3' direction of: C'-T-C'-T-X-C', at least one C' or T sequence may be missing one or more nucleotides. In the event that 2 or more nucleotides are missing, the missing nucleotides may be contiguous, or may be at separate locations. The one or more missing nucleotides may be, for example, between 1 and 10, 1 and 20, 1 100, or 1 and 1000 nucleotides.

In embodiments, in a method, reaction mixture, vessel, or kit provided herein involving a concatemer strand which comprises a nucleotide sequence having the general structure in the 5' to 3' direction of: C'-T-C'-T-X-C', at least one C' or T sequence may have one or more point mutations. In the event that two or more point mutations are present, the point mutations may be contiguous, or may be at separate locations. The one or more point mutations may be, for example, between 1 and 10, 1 and 20, 1 and 100, or 1 and 1000 point mutations.

In embodiments, in a method, reaction mixture, vessel, or kit provided herein involving a concatemer strand which comprises a nucleotide sequence having the general structure in the 5' to 3' direction of: C'-T-C'-T-X-C', the nucleotide sequence has two or all three of the following characteristics: i) between at least one C' and T, one or more extra nucleotides are present which are not part of the C' or T sequence; ii) at least one C' or T sequence is missing one or more nucleotides; and iii) at least one C' or T sequence contains one or more point mutations.

In embodiments, in a method, reaction mixture, vessel, or kit provided herein involving a concatemer strand which comprises a nucleotide sequence having the general structure in the 5' to 3' direction of: C'-T-C'-T-X-C', in embodiments which the polynucleotide template is an RNA molecule, the T may represent the nucleotide sequence of a DNA sequence which is analogous to the RNA sequence of the polynucleotide template.

In embodiments, in a method, reaction mixture, vessel, or kit provided herein involving a concatemer strand which comprises a nucleotide sequence having the general structure in the 5' to 3' direction of: C'-T-C'-T-X-C', the concatemer strand further comprises one or more nucleotides to the 5' of the 5'-most situated C' sequence. The one or more nucleotides may be, for example, between 1 and 10, 1 and 20, 1 and 100, or 1 and 1000 nucleotides.

In embodiments, in a method, reaction mixture, vessel, or kit provided herein involving a concatemer strand which comprises a nucleotide sequence having the general structure in the 5' to 3' direction of: C'-T-C'-T-X-C', the concatemer strand further comprises one or more nucleotides to the 3' of the 3'-most situated C' sequence. The one or more nucleotides may be, for example, between 1 and 10, 1 and 20, 1 and 100, or 1 and 1000 nucleotides.

In embodiments, provided herein is a method of generating a concatemer comprising at least two copies of a double stranded nucleic acid template, the method comprising: incubating in a reaction mixture at least a first template molecule and a second template molecule, wherein: the first template molecule comprises a first nucleic acid strand and a second nucleic acid strand, wherein: the first nucleic acid strand of the first template molecule comprises a nucleotide sequence having the general structure in the 5' to 3' direction of: H'-S-$Y_1$-H', wherein: H' represents the nucleotide sequence of a first homology sequence, S represents the nucleotide sequence of a first strand of the double stranded nucleic acid template, and $Y_1$ represents any number and sequence of nucleotides; and the second nucleic acid strand of the first template molecule comprises a nucleotide sequence having the general structure in the 5' to 3' direction of: H-$Y_1$'-S'-H, wherein: H represents the nucleotide sequence of a second homology sequence, wherein the first homology sequence and second homology sequence are complementary to each other, $Y_1$' represents a nucleotide sequence which is complementary to the nucleotide sequence of $Y_1$, and S' represents the nucleotide sequence of a second strand of the double stranded nucleic acid template, wherein the first strand and second strand of the double stranded nucleic acid template are complementary to each other; and the second template molecule comprises a first nucleic acid strand and a second nucleic acid strand, wherein: the first nucleic acid strand of the second template molecule comprises a nucleotide sequence having the general structure in the 5' to 3' direction of: H'-S-$Y_2$-H', wherein: H' represents the nucleotide sequence of the first homology sequence, S represents the nucleotide sequence of the first strand of the double stranded nucleic acid template, and $Y_2$ represents any number and sequence of nucleotides; and the second nucleic acid strand of the first template molecule comprises a nucleotide sequence having the general structure in the 5' to 3' direction of: H-$Y_2$'-S'-H, wherein: H represents the nucleotide sequence of the second homology sequence, $Y_2$' represents a nucleotide sequence which is complementary to the nucleotide sequence of $Y_2$, and S' represents the nucleotide sequence of the second strand of the double stranded nucleic acid template; and upon incubation of the first template molecule with the second template molecule in the reaction mixture, at least one concatemer comprising at least two copies of the double stranded nucleic acid template is formed, wherein the concatemer comprises a first concatemer strand and a second concatemer strand, wherein the first concatemer strand comprises a 5' end and a 3' end, and comprises a nucleotide sequence having the general structure in the 5' to 3' direction of: H'-S-$Y_2$-H'-S-$Y_1$-H', wherein each of H', $Y_1$, S, and $Y_2$ represent nucleotide sequences as described above; and wherein the second concatemer strand comprises a 5' end and a 3' end, and comprises a sequence having the general structure in the 5' to 3' direction of: H-$Y_1$'-S'-H-$Y_2$'-S'-H, wherein each of H', $Y_1$, S, and $Y_2$ represent nucleotide sequences as described above.

In embodiments, in a method, reaction mixture, vessel, or kit provided herein involving a first concatemer strand which comprises a nucleotide sequence having the general structure in the 5' to 3' direction of: H'-S-$Y_2$-H'-S-$Y_1$-H', at least one of or both $Y_1$ and $Y_2$ may represent 0 nucleotides.

In embodiments, in a method, reaction mixture, vessel, or kit provided herein involving a first concatemer strand which comprises a nucleotide sequence having the general structure in the 5' to 3' direction of: H'-S-$Y_2$-H'-S-$Y_1$-H', $Y_1$ may contain a sequence having the general structure in the 5' to 3' direction of [(H'-S)$_{N1}$] wherein H' and S represent nucleotide sequences as described above, and N1 is any integer between 0 and 2000.

In embodiments, in a method, reaction mixture, vessel, or kit provided herein involving a first concatemer strand which comprises a nucleotide sequence having the general structure in the 5' to 3' direction of: H'-S-$Y_2$-H'-S-$Y_1$-H', $Y_2$ may contain a sequence having the general structure in the 5' to 3' direction of [(H'-S)$_{N2}$] wherein H' and S represent nucleotide sequences as described above, and N2 is any integer between 0 and 2000.

In embodiments, in a method, reaction mixture, vessel, or kit provided herein involving a first template molecule and a second template molecule, the first template molecule and second template molecule are both double-stranded DNA molecules.

In embodiments, in a method, reaction mixture, vessel, or kit provided herein involving a first nucleic acid strand of a first template molecule comprises, wherein the first nucleic acid strand comprises a nucleotide sequence having the general structure in the 5' to 3' direction of: H'-S-Y$_1$-H', wherein H' represents the nucleotide sequence of a first homology sequence, the first homology sequence may contain no more than 4, 5, 6, 7, 8, 9, 10, 11, 12, 13, 14, 15, 20, 25, 30, 40, 50, 60, 70, 80, 90, or 100 nucleotides. In embodiments, the first homology sequence may contain at least 4, 5, 6, 7, 8, 9, 10, 11, 12, 13, 14, 15, 20, 25, 30, 40, 50, 60, 70, 80, 90, or 100 nucleotides. In embodiments, the first homology sequence may contain at least 4, 5, 6, 7, 8, 9, 10, 11, 12, 13, 14, 15, 20, 25, 30, 40, 50, 60, 70, 80, 90, or 100 and no more than 5, 6, 7, 8, 9, 10, 11, 12, 13, 14, 15, 20, 25, 30, 40, 50, 60, 70, 80, 90, 100, or 200 nucleotides.

In embodiments, a reaction mixture, vessel, or kit provided herein comprises a nucleic acid polymerase. In embodiments, a nucleic acid polymerase is a DNA polymerase having strand-displacement activity. In embodiments, a nucleic acid polymerase is an RNA polymerase. In embodiments, a nucleic acid polymerase is a reverse transcriptase. In embodiments, a reaction mixture, vessel, or kit comprises more than one kind of nucleic acid polymerase, such as both a DNA polymerase having strand displacement activity and a reverse transcriptase. In embodiments, a reaction mixture, vessel, or kit provided herein comprises nucleotides and buffer.

In embodiments, in a method, reaction mixture, vessel, or kit provided herein involving a polynucleotide template, the polynucleotide template is a single-stranded molecule. In embodiments, in a method, reaction mixture, vessel, or kit provided herein involving a polynucleotide template, the polynucleotide template comprises one strand of a double-stranded nucleic acid template. In embodiments, in a method, reaction mixture, vessel, or kit provided herein involving a polynucleotide template, the polynucleotide template is a DNA or RNA molecule.

In embodiments, in a method, reaction mixture, vessel, or kit provided herein involving a nucleic acid template, the nucleic acid template is an RNA or DNA molecule. In embodiments, a nucleic acid template may be a single-stranded or double-stranded molecule.

In embodiments, in a method provided herein involving incubation of a reaction mixture, during the incubation of the reaction mixture, the temperature of the reaction mixture does not exceed 90, 85, 80, 75, 70, 65, 60, 55, 50, 45, 40, 37, 35, 30, 25, or 20 C. In embodiments, in a method provided herein, all steps of the method are performed at a temperature of no greater than 90, 85, 80, 75, 70, 65, 60, 55, 50, 45, 40, 37, 35, 30, 25, or 20 C. In embodiments, a reaction mixture, vessel, or kit provided herein is maintained at a temperature of no greater than 90, 85, 80, 75, 70, 65, 60, 55, 50, 45, 40, 37, 35, 30, 25, or 20 C. In embodiments, a method provided herein is performed without thermocycling.

In embodiments, in a method, reaction mixture, vessel, or kit provided herein involving a polynucleotide template comprising a first portion, the first portion contains no more than 5, 10, 15, 20, 25, 30, 35, 40, 50, 60, 70, 80, 90, 100, or 200 nucleotides. In embodiments, in a method, reaction mixture, vessel, or kit provided herein involving a polynucleotide template comprising a first portion, the first portion contains at least 5, 10, 15, 20, 25, 30, 35, 40, 50, 60, 70, 80, 90, 100, or 200 nucleotides. In embodiments, in a method, reaction mixture, vessel, or kit provided herein involving a polynucleotide template comprising a first portion, the first portion contains at least 5, 10, 15, 20, 25, 30, 35, 40, 50, 60, 70, 80, 90, or 100 and no more than 10, 15, 20, 25, 30, 35, 40, 50, 60, 70, 80, 90, 100, or 200 nucleotides.

In embodiments, in a method, reaction mixture, vessel, or kit provided herein involving a primer comprising a first region, the first region contains at least 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a first region, the first region contains no more than 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a first region, the first region contains at least 4, 5, 6, 7, 8, 9, 10, 11, 12, 13, 14, 15, 20, 25, 30, 35, 40, 50, 60, 70, 80, or 90 and no more than 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a first primer comprising a first region and a second primer comprising a first region, both the first primer and second primer may have any of the features described above. In embodiments, in a method, reaction mixture, vessel, or kit provided herein involving a first primer comprising a first region and a second primer comprising a first region, the first region of the first primer and the first region of the second primer may contain the same number of nucleotides. In embodiments, in a method, reaction mixture, vessel, or kit provided herein involving a first primer comprising a first region and a second primer comprising a first region, the first region of the first primer and the first region of the second primer may contain a different number of nucleotides.

In embodiments, in a method, reaction mixture, vessel, or kit provided herein involving a primer comprising a second region, the second region contains at least 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a second region, the second region contains no more than 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a second region, the second region contains at least 4, 5, 6, 7, 8, 9, 10, 11, 12, 13, 14, 15, 20, 25, 30, 35, 40, 50, 60, 70, 80, or 90 and no more than 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a first primer comprising a second region and a second primer comprising a second region, both the first primer and second primer may have any of the features described above. In embodiments, in a method, reaction mixture, vessel, or kit provided herein involving a first primer comprising a second region and a second primer comprising a second region, the second region of the first primer and the second region of the second primer may contain the same number of nucleotides. In embodiments, in a method, reaction mixture, vessel, or kit provided herein involving a first primer comprising a second region and a second primer comprising a second region, the second region of the first primer and the second region of the second primer may contain a different number of nucleotides.

In embodiments, in a method, reaction mixture, vessel, or kit provided herein involving a second primer containing a second region and a polynucleotide template comprising a second portion, the nucleotide sequence of the second region of the second primer is the same as the nucleotide sequence of the second portion of the polynucleotide template.

In embodiments, in a method, reaction mixture, vessel, or kit provided herein involving a primer comprising a tail region, the tail region contains at least 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a tail region, the tail region contains no more than 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a tail region, the tail region contains at least 4, 5, 6, 7, 8, 9, 10, 11, 12, 13, 14, 15, 20, 25, 30, 35, 40, 50, 60, 70, 80, or 90 and no more than 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a first primer comprising a tail region and a second primer comprising a tail region, both the first primer and second primer may have any of the features described above. In embodiments, in a method, reaction mixture, vessel, or kit provided herein involving a first primer comprising a tail region and a second primer comprising a tail region, the tail region of the first primer and the tail region of the second primer may contain the same number of nucleotides. In embodiments, in a method, reaction mixture, vessel, or kit provided herein involving a first primer comprising a tail region and a second primer comprising a tail region, the tail region of the first primer and the tail region of the second primer may contain a different number of nucleotides.

In embodiments, in a method, reaction mixture, vessel, or kit provided herein involving a primer comprising a template-binding region, the template-binding region contains at least 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a template-binding region, the template-binding region contains no more than 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a template-binding region, the template-binding region contains at least 4, 5, 6, 7, 8, 9, 10, 11, 12, 13, 14, 15, 20, 25, 30, 35, 40, 50, 60, 70, 80, 90, or 100 and no more than 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a first primer comprising a template-binding region and a second primer comprising a template-binding region, both the first primer and second primer may have any of the features described above. In embodiments, in a method, reaction mixture, vessel, or kit provided herein involving a first primer comprising a template-binding region and a second primer comprising a template-binding region, the template-binding region of the first primer and the template-binding region of the second primer may contain the same number of nucleotides. In embodiments, in a method, reaction mixture, vessel, or kit provided herein involving a first primer comprising a template-binding region and a second primer comprising a template-binding region, the template-binding region of the first primer and the template-binding region of the second primer may contain a different number of nucleotides.

In embodiments, in a method, reaction mixture, vessel, or kit provided herein involving a polynucleotide template, the polynucleotide template may contain at least 8, 9, 10, 11, 12, 13, 14, 15, 20, 25, 30, 35, 40, 50, 60, 70, 80, 90, 100, 200, 500, 1000, 2000, or 5000 nucleotides. In embodiments, in a method, reaction mixture, vessel, or kit provided herein involving a polynucleotide template, the polynucleotide template may contain no more than 8, 9, 10, 11, 12, 13, 14, 15, 20, 25, 30, 35, 40, 50, 60, 70, 80, 90, 100, 200, 500, 1000, 2000, 5000, or 10,000 nucleotides. In embodiments, in a method, reaction mixture, vessel, or kit provided herein involving a polynucleotide template, the polynucleotide template may contain at least 8, 9, 10, 11, 12, 13, 14, 15, 20, 25, 30, 35, 40, 50, 60, 70, 80, 90, 100, 200, 500, 1000, 2000, or 5000, and no more than 9, 10, 11, 12, 13, 14, 15, 20, 25, 30, 35, 40, 50, 60, 70, 80, 90, 100, 200, 500, 1000, 2000, 5000, or 10,000 nucleotides.

In embodiments, in a method, reaction mixture, vessel, or kit provided herein involving a double-stranded nucleic acid template, each strand of the double-stranded nucleic acid template may contain at least 8, 9, 10, 11, 12, 13, 14, 15, 20, 25, 30, 35, 40, 50, 60, 70, 80, 90, 100, 200, 500, 1000, 2000, or 5000 nucleotides. In embodiments, in a method, reaction mixture, vessel, or kit provided herein involving a double-stranded nucleic acid template, each strand of the double-stranded nucleic acid template may contain no more than 8, 9, 10, 11, 12, 13, 14, 15, 20, 25, 30, 35, 40, 50, 60, 70, 80, 90, 100, 200, 500, 1000, 2000, 5000, or 10,000 nucleotides. In embodiments, in a method, reaction mixture, vessel, or kit provided herein involving a double-stranded nucleic acid template, each strand of the double-stranded nucleic acid template may contain at least 8, 9, 10, 11, 12, 13, 14, 15, 20, 25, 30, 35, 40, 50, 60, 70, 80, 90, 100, 200, 500, 1000, 2000, or 5000, and no more than 9, 10, 11, 12, 13, 14, 15, 20, 25, 30, 35, 40, 50, 60, 70, 80, 90, 100, 200, 500, 1000, 2000, 5000, or 10,000 nucleotides.

In embodiments, a reaction mixture, vessel, or kit provided herein does not contain a recombinase enzyme.

In embodiments, in a method, reaction mixture, vessel, or kit provided herein may contain or involve multiple copies of a primer. The multiple copies may be, for example, at least 5, 10, 15, 20, 50, 100, 500, 1000, 10,000, 100,000, or 1,000,000 copies of the primer.

In embodiments, a reaction mixture or vessel provided herein may comprise at least a portion of a biological sample from a subject. The biological sample may be, for example, saliva, blood, urine, a cheek swab, or a nasal swab. The subject may be a human.

In some embodiments, all of the steps of a method provided herein are performed at a temperature of no greater than 70, 65, 60, 65, 60, 55, 50, 45, 40, 35, 30, 25, 20, 15, or 10 C. In some embodiments, some of the steps of a method provided herein are performed at a temperature of no greater than 70, 65, 60, 65, 60, 55, 50, 45, 40, 35, 30, 25, 20, 15, or 10 C.

In some embodiments, two or more steps of a method provided herein are performed simultaneously in the same reaction mixture. In some embodiments, all of the steps of a method provided herein are performed simultaneously in the same reaction mixture.

In some embodiments, in a method provided herein, a nucleic acid template is amplified at least 10, 100, 1000, 10,000, 100,000, or 1,000,000-fold within 5, 10, 15, 20, 30, 40, 50, 60, 70, 80, 90, 120, or 180 minutes of initiation of the method. In some embodiments, in a method provided herein, the number of copies of a nucleic acid template in a reaction mixture is increased least 10, 100, 1000, 10,000, 100,000, or 1,000,000-fold within 5, 10, 15, 20, 30, 40, 50, 60, 70, 80, 90, 120, or 180 minutes of initiation of the method.

In embodiments, a nucleic acid template provided herein may be a single-stranded or a double-stranded nucleic acid template.

In embodiments, provided herein is a vessel, comprising in fluid communication therein: a first primer, wherein the first primer comprises a first region and a second region, and wherein the second region of the first primer comprises a nucleotide sequence which is complementary to a first portion of a polynucleotide template; a second primer, wherein the second primer comprises a first region and a second region, and wherein the second region of the second primer comprises a nucleotide sequence which is complementary to a partner nucleotide sequence, wherein the partner nucleotide sequence is complementary to a second portion of the polynucleotide template; and at least one concatemer strand, wherein the concatemer strand comprises a 5' end and a 3' end, and comprises a nucleotide sequence having the general structure in the 5' to 3' direction of: C'-T-C'-T-X-C', wherein: C' represents the nucleotide sequence of the first region of the second primer, T represents the nucleotide sequence of the polynucleotide template or an analogous sequence thereof, and X represents any number and sequence of nucleotides.

In some embodiments, provided herein is a vessel, comprising in fluid communication therein: (A) an isolated nucleic acid polymerase, (B) a nucleic acid template comprising at least a first strand, (C) a first primer comprising a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, wherein the template-binding region is complementary to a first strand of the nucleic acid template, and (D) a second primer comprising a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, and wherein the template-binding region is complementary to a nucleotide sequence complementary to first strand of the nucleic acid template, and wherein the tail region of the second primer contains a nucleotide sequence which is complementary to the nucleotide sequence of the tail region of the first primer, if the sequences of the primers are aligned such that the 5' terminal nucleotide of the second primer is aligned with the innermost nucleotide of the tail region of the first primer and the 5' terminal nucleotide of the first primer is aligned with the innermost nucleotide of the tail region of the second primer.

In embodiments, provided herein is a kit comprising two or more fluidically isolated containers, the containers collectively comprising: a first primer, wherein the first primer comprises a first region and a second region, and wherein the second region of the first primer comprises a nucleotide sequence which is complementary to a first portion of a polynucleotide template; a second primer, wherein the second primer comprises a first region and a second region, and wherein the second region of the second primer comprises a nucleotide sequence which is complementary to a partner nucleotide sequence, wherein the partner nucleotide sequence is complementary to a second portion of the polynucleotide template; and an isolated DNA polymerase having strand-displacement activity; wherein: the first region of the first primer and the first region of the second primer are complementary.

In some embodiments, provided herein is a kit for detecting a target nucleic acid of interest comprising at least a first strand, the kit comprising two or more fluidically isolated containers, the containers collectively comprising: (A) an isolated nucleic acid polymerase, (B) a first primer comprising a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, wherein the template-binding region is complementary to the first strand of the target nucleic acid, and (C) a second primer comprising a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, and wherein the template-binding region is complementary to a nucleotide sequence complementary to the first strand of the target nucleic acid, and wherein the tail region of the second primer contains a nucleotide sequence which is complementary to the nucleotide sequence of the tail region of the first primer, if the sequences of the primers are aligned such that the 5' terminal nucleotide of the second primer is aligned with the innermost nucleotide of the tail region of the first primer and the 5' terminal nucleotide of the first primer is aligned with the innermost nucleotide of the tail region of the second primer.

In some embodiments, a kit provided herein comprises a nucleic acid having the nucleotide sequence of the target nucleic acid of interest.

In some embodiments, a reaction mixture, vessel or kit provided herein comprises a nucleic acid dye.

In some embodiments, in a vessel or kit provided herein comprising an isolated nucleic acid polymerase, the isolated nucleic acid polymerase is a DNA polymerase. In some embodiments, in a vessel or kit provided herein comprising an isolated nucleic acid polymerase, the isolated nucleic acid polymerase is a reverse transcriptase. In some embodiments, in a vessel or kit provided herein comprising an isolated nucleic acid polymerase, the vessel or kit comprises both a DNA polymerase and a reverse transcriptase.

In some embodiments, in a method, vessel, or kit provided herein comprising a nucleic acid polymerase, the nucleic acid polymerase has strand displacement activity.

In some embodiments, a method provided herein comprises treating one or more of the reaction components or steps of the method with a nucleic acid dye.

In some embodiments, in a method, vessel, or kit provided herein comprising a nucleic acid template, the template is a DNA molecule. In some embodiments, in a method, vessel, or kit provided herein comprising a nucleic acid template, the template is an RNA molecule.

In some embodiments, in a method, vessel, or kit provided herein comprising a first primer, the tail region of the first primer comprises at least 4, 5, 6, 7, 8, 9, 10, 11, 12, 13, 14, 15, 16, 17, 18, 19, or 20 nucleotides. In some embodiments, in a method, vessel, or kit provided herein comprising a first primer, the tail region of the first primer comprises no more than 4, 5, 6, 7, 8, 9, 10, 11, 12, 13, 14, 15, 16, 17, 18, 19, 20, 30, 40, 50, or 60 nucleotides.

In some embodiments, in a method, vessel, or kit provided herein comprising a second primer, the tail region of the second primer comprises at least 4, 5, 6, 7, 8, 9, 10, 11, 12, 13, 14, 15, 16, 17, 18, 19, or 20 nucleotides. In some embodiments, in a method, vessel, or kit provided herein comprising a second primer, the tail region of the second primer comprises no more than 4, 5, 6, 7, 8, 9, 10, 11, 12, 13, 14, 15, 16, 17, 18, 19, 20, 30, 40, 50, or 60 nucleotides.

In some embodiments, in a method, vessel, or kit provided herein comprising a first primer, the template-binding region of the first primer comprises at least 4, 5, 6, 7, 8, 9, 10, 11, 12, 13, 14, 15, 16, 17, 18, 19, or 20 nucleotides. In some embodiments, in a method, vessel, or kit provided herein comprising a first primer, the template-binding region of the first primer comprises no more than 4, 5, 6, 7, 8, 9, 10, 11, 12, 13, 14, 15, 16, 17, 18, 19, 20, 30, 40, 50, or 60 nucleotides.

In some embodiments, in a method, vessel, or kit provided herein comprising a second primer, the template-binding region of the second primer comprises at least 4, 5, 6, 7, 8, 9, 10, 11, 12, 13, 14, 15, 16, 17, 18, 19, or 20 nucleotides. In some embodiments, in a method, vessel, or kit provided herein comprising a second primer, the template-binding region of the second primer comprises no more than 4, 5, 6, 7, 8, 9, 10, 11, 12, 13, 14, 15, 16, 17, 18, 19, 20, 30, 40, 50, or 60 nucleotides.

In some embodiments, in methods and compositions provided herein wherein an RNA molecule is the template molecule or primary nucleic acid, amplification of the template may refer to generation of copies of DNA strands corresponding to the RNA molecule.

In some embodiments, a method provided herein comprises measuring a fluorescent signal from an assay comprising the method.

In some embodiments, a nucleic acid ligase may be included with a method or composition provided herein. In some embodiments, a nucleic acid template may be amplified more rapidly with a method provided herein when a ligase is included in a reaction mixture for a method provided herein, as compared to if a nucleic acid ligase is not included in the reaction. In embodiments, a reaction mixture, vessel, or kit provided herein may contain an enzyme having ligase activity.

In embodiments, provided herein is a method of assaying for a pathogen in a sample, the method comprising performing a method as provided herein to amplify nucleic acid from the pathogen. In embodiments, the target nucleic acid used in a composition or method provided herein may be nucleic acid from a pathogen. In embodiments, the first and second primer used in a method provided herein may each contain regions which are complementary to a sequence in the nucleic acid of the pathogen, or which are complementary to a sequence which is complementary to a sequence in the nucleic acid of the pathogen. In embodiments, the nucleic acid of the pathogen may be DNA or RNA. Pathogens may include, without limitation, viruses, bacteria, fungi, and protists. A sample may be from a subject, and may have any of the sample characteristics described elsewhere herein.

In embodiments, a method provided herein for amplification of a nucleic acid may be used for a diagnostic method externally of a human or animal body. For example, a sample may be obtained from a human or animal, and the sample may be assayed for a target nucleic acid of interest with a method provided herein for amplification of nucleic acid.

In embodiments, a method provided herein may include: a) providing one or more reagents for performing a method as provided herein (e.g. one or more of first primer, second primer, nucleic acid template, nucleic acid polymerase, nucleotides, buffer, water, etc.) in a reaction mixture, and b) incubating the reaction mixture at a substantially isothermal temperature, wherein the temperature of the reaction mixture does not diverge from a central temperature by more or less than 20, 15, 10, 9, 8, 7, 6, 5, 4, 3, 2, or 1 degree Celsius during the incubation. In embodiments, a central temperature may be, for example, 30, 35, 40, 45, 50, 55, 60, 65, 70, 75, or 80 degrees Celsius.

In embodiments, a method provided herein may be performed at a substantially isothermal temperature. In embodiments, a substantially isothermal temperature may be any of 30, 35, 40, 45, 50, 55, 60, 65, 70, 75, or 80 degrees Celsius, plus or minus 20, 15, 10, 9, 8, 7, 6, 5, 4, 3, 2, or 1 degree Celsius.

In embodiments, a method provided herein may be performed at one or more temperatures, none or which exceed 90, 85, 80, 75, 70, 65, 60, 55, 50, 45, 40, 35, 30, or 25 degrees Celsius.

In embodiments, methods provided herein may be performed without thermocycling/reaction mixtures may be incubated under conditions without thermocycling (i.e. without cycles of raising and lowering incubation temperatures to separate strands or allow hybridization of primers as is used in, for example, PCR-based methods).

In compositions and methods provided herein involving a first primer comprising a first region and a second primer comprising a first region, wherein the first region of the first primer is complementary to the first region of the second primer, in embodiments, the first region of the first primer and the first region of the second primer contain nucleotide sequences such that a double stranded structure which would be formed by the annealing of the first region of the first primer to the first region of the second primer according to Watson-Crick base pairing rules would not form a restriction enzyme recognition sequence.

In compositions and methods provided herein involving a nucleic acid polymerase, in embodiments, the nucleic acid polymerase has 3' to 5' exonuclease activity.

In embodiments, provided herein is a method for amplifying a target nucleic acid strand, the method comprising: incubating a reaction mixture comprising the target nucleic acid strand, a first primer, and a second primer under substantially isothermal conditions, wherein: the target nucleic acid strand comprises a first portion and a second portion; the first primer comprises a first region and a second region, wherein the first region comprises a 5' end of the primer, the second region comprises a 3' end of the primer, and the second region is complementary to the first portion of the nucleic acid strand; the second primer comprises a first region and a second region, wherein the first region comprises a 5' end of the primer, the second region comprises a 3' end of the primer, and the second region is complementary to a sequence which is complementary to the second portion of the nucleic acid strand; the first region of the first primer is complementary to the first region of the second primer; and the target nucleic acid strand is amplified. Optionally, the target nucleic acid strand may further comprise a third portion, wherein the third portion is situated in the target nucleic acid strand between the first portion and the second portion, and wherein the first region of the second primer is complementary to the third portion of the target nucleic acid strand.

In embodiments, in any of the methods provided herein, a, polynucleotide template, target nucleic acid strand or the like may contain an internal motif, wherein the tail region of a primer provided herein to amplify the target nucleic acid strand is complementary to the internal motif.

In embodiments, a method provided herein may further comprise adding to a reaction mixture provided herein a peptide-nucleic acid (PNA) probe and a dye which binds to DNA-PNA hybrid, wherein the PNA probe is complementary to a target nucleic acid for amplification in the reaction mixture, or a complement thereof.

In embodiments, a reaction mixture provided herein may comprise a DNA polymerase having strand-displacement activity.

When a nucleic acid is described herein as being "amplified" or the like, the nucleic acid may also be described as being "copied" or the like.

In embodiments, in a primer described herein as having a first region and a second region, the first region may contain the 5' end of the primer and the second region may contain the 3' end of the primer.

In embodiments, in a primer described herein as having a tail region and a template-binding region, the first region may contain the 5' end of the primer and the second region may contain the 3' end of the primer.

In embodiments, provided herein is method for copying a polynucleotide template, the method comprising: incubating a reaction mixture comprising the polynucleotide template, a first primer, and a second primer under conditions without thermocycling, wherein: the polynucleotide template comprises a first portion and a second portion; the first primer comprises a first region and a second region, wherein the first region comprises a 5' end of the primer, the second region comprises a 3' end of the primer, and the second region is complementary to the first portion of the polynucleotide template; the second primer comprises a first region and a second region, wherein the first region comprises a 5' end of the primer, the second region comprises a 3' end of the primer, and the second region is complementary to a sequence which is complementary to the second portion of the polynucleotide template; the first region of the first primer is complementary to the first region of the second primer; and multiple copies of the polynucleotide template are generated. Optionally, the polynucleotide template may further comprise a third portion, wherein the third portion is situated in the polynucleotide template between the first portion and the second portion, and wherein the first region of the second primer is complementary to the third portion of the polynucleotide template.

In embodiments, provided herein is a method for amplifying a polynucleotide template, the method comprising incubating the polynucleotide template in a reaction mixture comprising a first primer and a second primer, wherein: the polynucleotide template comprises a first portion, a second portion and a third portion, wherein the third portion is situated in the polynucleotide template between the first portion and the second portion; the first primer comprises a first region and a second region, wherein the second region of the first primer is complementary to the first portion of the polynucleotide template; and the second primer comprises a first region and a second region, wherein the second region of the second primer is complementary to a sequence which is complementary to the second portion of the polynucleotide template, the first region of the second primer is complementary to the first region of the first primer, and the first region of the second primer is complementary to the third portion of the polynucleotide template.

In embodiments, provided herein is a method for assessing the identity of a nucleotide at a position of interest in a nucleotide sequence in a polynucleotide template, the method comprising: A) providing copies of the polynucleotide template in each of at least a first reaction mixture and a second reaction mixture, wherein: the polynucleotide template comprises a first portion, a second portion and a third portion, wherein the third portion is situated in the polynucleotide template between the first portion and the second portion and wherein the position of interest is in the third portion; the first reaction mixture comprises copies of the polynucleotide template, a first primer, and a second primer, wherein: the first primer comprises a first region and a second region, wherein the first region comprises a 5' end of the primer, the second region comprises a 3' end of the primer, and the second region is complementary to a first portion of the polynucleotide template; the second primer comprises a first region and a second region, wherein the first region comprises a 5' end of the primer, the second region comprises a 3' end of the primer, and the second region is complementary to a sequence which is complementary to a second portion of the polynucleotide template; the first region of the first primer is complementary to the first region of the second primer; and the first region of the second primer is complementary to the third portion of the polynucleotide template; the second reaction mixture comprises copies of the polynucleotide template, a third primer, and a fourth primer, wherein: the third primer comprises a first region and a second region, wherein the first region comprises a 5' end of the primer, the second region comprises a 3' end of the primer, and the second region is complementary to a first portion of the polynucleotide template; the fourth primer comprises a first region and a second region, wherein the first region comprises a 5' end of the primer, the second region comprises a 3' end of the primer, and the second region is complementary to a sequence which is complementary to a second portion of the polynucleotide template; the first region of the third primer is complementary to the first region of the fourth primer; and the first region of the fourth primer is complementary to the third portion of the polynucleotide template; and the nucleotide sequence of the first region of the second primer differs from the nucleotide sequence of first region of the fourth primer by a single nucleotide, wherein the position of the different nucleotide in the second and fourth primers corresponds to the position of the nucleotide of interest in the polynucleotide template if the nucleotide sequence of the first region of the second primer or fourth primer is oriented with the nucleotide sequence of the third portion of the polynucleotide template for maximum complementation of the sequences; B) incubating the first reaction mixture and second reaction mixture under conditions without thermocycling; and C) comparing the rate or amount of amplification of the polynucleotide template in the first reaction mixture to the rate or amount of amplification of the polynucleotide template in the second reaction mixture, wherein the rate or amount of amplification of the polynucleotide template is indicative of the degree of complementation between first region of the second or fourth primer and the nucleotide sequence of the third portion of the polynucleotide template.

Optionally, in embodiments provided herein involving a polynucleotide template, the polynucleotide template is a DNA strand.

Optionally, in embodiments provided herein involving a polynucleotide template, the polynucleotide template is an RNA strand.

Optionally, in embodiments provided herein involving a polynucleotide template, the polynucleotide template is one strand of a duplex nucleic acid molecule. In embodiments, the duplex nucleic acid molecule is a duplex DNA molecule or a duplex RNA molecule.

Optionally, in embodiments provided herein involving a reaction mixture, vessel, or kit, the reaction mixture, vessel, or kit comprises a DNA polymerase having strand displacement activity.

Optionally, in embodiments provided herein involving a reaction mixture, vessel, or kit, the reaction mixture, vessel, or kit comprises a reverse transcriptase.

Optionally, in embodiments provided herein involving a reaction mixture, vessel, or kit, the reaction mixture, vessel, or kit comprises a nucleic acid dye, nucleotides, or buffers.

Optionally, in embodiments provided herein involving a polynucleotide template containing a first portion, a second portion, and a third portion, the polynucleotide template may have the general structure of elements, in the 3' to 5' direction, of: 1P-1S-3P-2S-2P, wherein "1P" is the first portion, "1 S" is a first space, "3P" is the third portion, "2S" is a second space, and "2P" is the second portion. The "first space" and "second space" are portions of the polynucleotide template which contain nucleotides which are not part of the first portion, second portion, or third portion. In embodiments, the first portion may have, for example, between 6 and 30 nucleotides or any other number of nucleotides as described elsewhere herein. In embodiments, the first space may, for example, between 2 and 30 nucleotides or any other number of nucleotides as described elsewhere herein. In embodiments, the third portion may have, for example, between 4 and 14 nucleotides or any other number of nucleotides as described elsewhere herein. In embodiments, the first space may, for example, between 2 and 30 nucleotides or any other number of nucleotides as described elsewhere herein. In embodiments, the first portion may have, for example, between 6 and 30 nucleotides or any other number of nucleotides as described elsewhere herein.

In embodiments, in methods provided herein involving the incubation of a polynucleotide template in a reaction mixture, a concatemer strand comprising at least 2, 3, 4, 5, or 10 copies of the polynucleotide template may be generated during the incubation of the reaction mixture.

In embodiments, provided herein is a method for amplifying a double stranded nucleic acid molecule, the method comprising incubating the double stranded nucleic acid molecule in a reaction mixture comprising a first primer and a second primer, wherein: the double stranded nucleic acid molecule comprises a first strand and a second strand, wherein the first strand comprises a first portion and a third portion and the second strand comprises a second portion; the first primer comprises a first region and a second region, wherein the second region of the first primer is complementary to the first portion of the first strand; and the second primer comprises a first region and a second region, wherein the second region of the second primer is complementary to the second portion of the second strand, the first region of the second primer is complementary to the third portion of the first strand, and the first region of the second primer is complementary to the first region of the first primer.

In embodiments, provided herein is a reaction mixture comprising: a polynucleotide template, a first primer, and a second primer, wherein: the polynucleotide template comprises a first portion, a second portion and a third portion, wherein the third portion is situated in the polynucleotide template between the first portion and the second portion; the first primer comprises a first region and a second region, wherein the first region comprises a 5' end of the primer, the second region comprises a 3' end of the primer, and the second region is complementary to the first portion of the polynucleotide template; the second primer comprises a first region and a second region, wherein the first region comprises a 5' end of the primer, the second region comprises a 3' end of the primer, and the second region is complementary to a sequence which is complementary to the second portion of the polynucleotide template; the first region of the first primer is complementary to the first region of the second primer; and the first region of the second primer is complementary to the third portion of the polynucleotide template.

In embodiments, provided herein is a kit for the amplification of a polynucleotide template, the kit comprising: a first primer and a second primer, wherein: the first primer comprises a first region and a second region, wherein the first region comprises a 5' end of the primer, the second region comprises a 3' end of the primer, and the second region is complementary to a first portion of the polynucleotide template; the second primer comprises a first region and a second region, wherein the first region comprises a 5' end of the primer, the second region comprises a 3' end of the primer, and the second region is complementary to a sequence which is complementary to a second portion of the polynucleotide template; the first region of the first primer is complementary to the first region of the second primer; and the first region of the second primer is complementary to a third portion of the polynucleotide template, wherein the third portion is situated in the polynucleotide template between the first portion and the second portion.

Optionally, in embodiments provided herein involving a kit, the components of the kit may be distributed between at least two separate fluidically isolated containers.

In embodiments, provided herein is a kit comprising two or more fluidically isolated containers, the containers collectively comprising: a first primer, a second primer, a third primer, and a fourth primer, wherein: the first primer comprises a first region and a second region, wherein the first region comprises a 5' end of the primer, the second region comprises a 3' end of the primer, and the second region is complementary to a first portion of a polynucleotide template; the second primer comprises a first region and a second region, wherein the first region comprises a 5' end of the primer, the second region comprises a 3' end of the primer, and the second region is complementary to a sequence which is complementary to a second portion of the polynucleotide template; the third primer comprises a first region and a second region, wherein the first region comprises a 5' end of the primer, the second region comprises a 3' end of the primer, and the second region is complementary to the first portion of the polynucleotide template; the fourth primer comprises a first region and a second region, wherein the first region comprises a 5' end of the primer, the second region comprises a 3' end of the primer, and the second region is complementary to a sequence which is complementary to a second portion of the polynucleotide template; the first region of the first primer is complementary to the first region of the second primer; the first region of the third primer is complementary to the first region of the fourth primer; and the nucleotide sequence of the first region of the first primer differs from the nucleotide sequence of first region of the third primer by a single nucleotide. Optionally, the first region of the second primer and the first region of the fourth primer are both complementary to a third portion of the polynucleotide template, wherein the third portion is situated in the polynucleotide template between the first portion and the second portion. Optionally, the second region of the each of the first primer, second primer, third primer, and fourth primers is between 6 and 30 nucleotides in length. Optionally, the second region of the each of the first primer, second primer, third primer, and fourth primers is between 6 and 30 nucleotides in length.

In embodiments provided herein involving a kit, the kit may comprises a control nucleic acid strand comprising the nucleotide sequence of a polynucleotide template to be detected with reagents of the kit.

In methods and compositions provided herein, optionally, a PNA probe and the dye $DiSc_2(5)$ may be included. The PNA probe may specifically anneal to a target sequence for amplification in the relevant reaction, and copies thereof, such that DNA-PNA duplexes are formed. Methods provided herein may include detecting a color change of the dye $DiSc_2(5)$ upon the binding of the dye to DNA-PNA duplexes. In embodiments, a PNA probe and dye may be added to a reaction mixture provided herein after the initiation or after the completion of the reaction. In embodiments, a PNA probe and dye may be added to a reaction mixture provided herein at least 5, 10, 15, 20, 30, 40, 50, 60, 70, 80, 90 or 100 minutes after the initiation of the reaction. In embodiments, a PNA probe and dye may be added to a reaction mixture provided herein no more than 5, 10, 15, 20, 30, 40, 50, 60, 70, 80, 90, or 100 minutes after the initiation of the reaction.

References herein to generating a copy of or amplifying a polynucleotide template or nucleic acid template include generating a copy which contains the sequence of the polynucleotide template/nucleic acid template, as well as generating a copy which contains an analogous sequence of the polynucleotide template/nucleic acid template, unless the context clearly dictates otherwise. For instance, if a polynucleotide template is RNA, generating a copy of the template can include generating a copy which is a DNA molecule which contains the DNA version of the RNA sequence of the polynucleotide template (i.e. in the DNA sequence, contains "T"s instead of "U"s).

In some embodiments, a method or composition provided herein may be used to detect the presence or absence of a particular nucleotide of interest in a target nucleic acid (e.g. in the case of a mutation or SNP). For example, a first or second primer may be selected which selectively binds to a region in a target nucleic acid which includes or is adjacent to the nucleotide of interest. The primer may be designed such that it selectively either: i) binds to the region when the region contains the nucleotide of interest, or ii) does not bind to the region when the region contains the nucleotide of interest. A method as described herein may be performed with the selected primer, and the outcome of the amplification reaction may provide information regarding the presence or absence of the nucleotide of interest in the target nucleic acid. For example, if the template-binding region of a first primer is designed to have a nucleotide sequence which is complementary to a sequence in the target nucleic acid which includes a particular nucleotide of interest (e.g. a mutation), successful amplification of the target nucleic acid with the selected primer from a sample may indicate that the sample contains a target nucleic acid having the particular nucleotide of interest. In some embodiments, a primer used for analysis of a nucleotide of interest in a target nucleic acid may contain a critical nucleotide (i.e. a nucleotide which corresponds to the same position of a nucleotide of interest in the target nucleic acid) at the 3' terminus of the primer. In such a case, the annealing of the 3' terminal nucleotide of the primer may be dependent on the presence of the nucleotide of interest in the target nucleic acid. If the 3' terminal nucleotide of the primer does not anneal with a nucleotide in the target nucleic acid (e.g. due to a mismatch between the nucleotides), the mismatch may significantly impair a nucleic acid polymerase from synthesizing an extension product from the primer. Accordingly, in some embodiments, a primer having a 3' terminal nucleotide which corresponds to a nucleotide of interest may be useful for determining the presence or absence of a particular nucleotide in a target nucleic acid. In such embodiments, in some situations the critical nucleotide at the 3' terminus of the primer may be selected to be complementary the nucleotide of interest in the target nucleic acid, and in some other situations the critical nucleotide at the 3' terminus of the primer may be selected to be non-complementary the nucleotide of interest in the target nucleic acid. The nucleotide of interest may represent, for example, a wild-type form, a mutant form, or a polymorphism of a target nucleic acid.

In other embodiments, a particular nucleotide of interest in a target nucleic acid (e.g. a mutation or SNP) may be detected by selecting primers such that the nucleotide of interest is present in the target nucleic acid in a region which is not complementary to a template-binding region of a first or second primer. For example, the nucleotide of interest may be approximately in the middle of a target nucleic acid sequence. In embodiments, the nucleotide of interest may be in an "internal motif" described elsewhere herein. When a nucleotide of interest is in an internal motif, in embodiments, a primer pair may be prepared to contain a nucleotide sequence in the tail region of the primers which is complementary to an internal motif or the complement thereof, and which may be used to assay for the presence or absence of the nucleotide of interest in the internal motif in the target sequence. As explained elsewhere herein, the temporary annealing of a nucleotide sequence in the tail region of a primer to an internal motif in an extension product of that primer may increase the rate of a reaction provided herein. In some circumstances, the greater the affinity of a nucleotide sequence in the tail region of a primer to the internal motif in an extension product of that primer, the faster the reaction may occur. Also, typically, the greater the number of nucleotides in the nucleotide sequence in the tail region of the primer which can bind to nucleotides in the internal motif in the extension product of the primer, the greater the affinity of the nucleotide sequence in the tail region of the extension product for the internal motif in the extension product. Thus, with compositions and methods provided herein, in embodiments, the presence or absence of a nucleotide of interest in a target sequence may be determined through the use of primers which have a nucleotide sequence in the tail region of the primer which can bind to the internal motif in the target sequence or a complement thereof, and which, within the tail region, do or do not have a nucleotide which specifically binds with the particular nucleotide of interest in the internal motif or its complement. Typically, the reaction will occur faster when the nucleotide sequence in the tail region of a primer contains a nucleotide which is complementary to the nucleotide in the extension product of that primer which corresponds to the nucleotide of interest in the target, than when the relevant nucleotide in the tail region of the primer is not complementary to the nucleotide in the extension product of that primer which corresponds to the nucleotide of interest in the target. For example, the internal motif of a wild-type version of a target nucleic acid strand may have the nucleotide sequence: 5' TATTGCAT 3'. However, the "G" in the sequence may frequently be mutated to an "A" in many individuals in the population. In order to determine whether a particular target nucleic acid contains a "G" or other nucleotide in the sequence, a primer may be prepared which contain a nucleotide sequence in its tail region having the sequence: 5'ATGCAATA 3'. If this primer (and an appropriate second primer) is used to amplify the target nucleic acid according to a method provided herein, the amplification reaction may have a certain reaction rate if the "G" is present in the internal motif, versus if a different nucleotide is present at the position of the "G" in the internal motif. This is because the nucleotide sequence in the tail region of the primer will be perfectly complementary to the internal motif if the "G" is present in the internal motif, but it will not be if a nucleotide other than a "G" is present at the G's normal position. Generally, in this example, if a "G" is present in the internal motif, the tail region of the primer will anneal to the internal motif more frequently than if the "G" is not present, and this may in turn lead to a faster reaction rate if the "G" is present than not present. With systems and methods provided herein, primers may be prepared to assay for either the presence or absence of a nucleotide of interest (e.g. primers can be prepared such that the reaction occurs more quickly if a mutated version of a nucleotide is present than if a wild-type version of the nucleotide is present, or vice-versa). Also, in embodiments, primers may be prepared so as to determine the identity of an unknown nucleotide in a position of interest in an internal motif in a target. For example, four different primer pairs may be prepared, each containing either an A, T, G, or C as appropriate corresponding to a nucleotide of interest in a target nucleic acid. In embodiments, the primer pair which yields the fastest reaction results may indicate which nucleotide is present in the position of interest in the internal motif in the target nucleic acid. For instance, a target nucleic acid may have an internal motif which commonly has the sequence, in the 5' to 3' direction of: GTAACGAG. However, different variants of the target nucleic acid may have different nucleotides in the $5^{th}$ position in the internal motif (i.e. the position of the "C"). Continuing with the example, if a sample containing the target nucleic acid is provided, wherein it is unknown what nucleotide is in the $5^{th}$ position in the of the internal motif, the sample can be divided into at least 4 portions, and the four portions can be used for a first reaction mixture, a second reaction mixture, a third reaction mixture, and a fourth reaction mixture. To the first reaction mixture, a first primer pair is provided, where the primers have tail regions with the sequences, in the 5' to 3' direction: CTCGTTAC and GTAACGAG, respectively. These tail regions will be perfectly complementary to the internal motif or complement thereof, if a "C" is present at $5^{th}$ position in internal motif. Thus, if the target is amplified most quickly in this reaction mixture, it indicates that a "C" is present in the position of the nucleotide of interest in the internal motif in the target. To the second reaction mixture, a second primer pair is provided, where the primers have tail regions with the sequences, in the 5' to 3' direction: CTCATTAC and GTAATGAG, respectively. These tail regions will be perfectly complementary to the internal motif or complement thereof, if a "T" is present at 5th position in internal motif. Thus, if the target is amplified most quickly in this reaction mixture, it indicates that a "T" is present in the position of the nucleotide of interest in the internal motif in the target. To the third reaction mixture, a third primer pair is provided, where the primers have tail regions with the sequences, in the 5' to 3' direction: CTCCTTAC and GTAAGGAG, respectively. These tail regions will be perfectly complementary to the internal motif or complement thereof, if a "G" is present at $5^{th}$ position in internal motif. Thus, if the target is amplified most quickly in this reaction mixture, it indicates that a "G" is present in the position of the nucleotide of interest in the internal motif in the target. To the fourth reaction mixture, a fourth primer pair is provided, where the primers have tail regions with the sequences, in the 5' to 3' direction: CTCTTTAC and GTAAAGAG, respectively. These tail regions will be perfectly complementary to the internal motif or complement thereof, if an "A" is present at $5^{th}$ position in internal motif. Thus, if the target is amplified most quickly in this reaction mixture, it indicates that an "A" is present in the position of the nucleotide of interest in the internal motif in the target. In embodiments, methods or compositions as generally described above may optionally be prepared with only 2 or 3 reaction mixtures with primer pairs corresponding to only 2 or 3 options for a nucleotide at a position of interest, if for example, it is not desired to screen all possible nucleotide variants (for instance if only 2 different nucleotides are typically found in a position of interest).

In embodiments, a sample containing a target nucleic acid may be divided into at least a first and a second portion, where the first portion is incubated in a first reaction mixture with a first primer pair, and the second portion is incubated in a second reaction mixture with a second primer pair, according to methods provided herein. In embodiments, the first primer pair and the second primer pair differ from each other by only a single nucleotide in the respective tail/first regions of the primer (e.g. the sequence of the first region of the first primer of the first pair differs from the sequence of the first region of the first primer of the second pair by only a single nucleotide). The single nucleotide which is different in the tail region of the primers may correspond to the position of a nucleotide of interest in the target nucleic acid. By comparing the rate or quantity of amplification of the target nucleic acid in the first reaction mixture to that in the second reaction mixture, the identity of a nucleotide of interest in the target nucleic acid may be determined. In embodiments, the method outlined above may be performed with a first, second, third, and fourth portion of the sample, and with a first primer pair, second primer pair, third primer pair, and fourth primer pair, wherein the first primer pair, second primer pair, third primer pair, and fourth primer pair differ from each other by only a single nucleotide in the respective tail/first region of the primers, as described above.

In embodiments, at least a first target nucleic acid and a second target nucleic acid may be provided, wherein the first target nucleic acid and the second target nucleic acid differ by a single nucleotide at a position of interest in an internal motif as described elsewhere herein. In embodiments, the first target nucleic acid may be incubated in a first reaction mixture containing a primer pair described herein and the second target nucleic acid may be incubated in a second reaction mixture containing the same primer pair, according to methods provided herein. By comparing the rate or quantity of amplification of the first target nucleic acid in the first reaction mixture to that of the second target nucleic acid in second reaction mixture or to an absolute value, the identity of the nucleotide in the position of interest in one or both of the first target nucleic acid and the second target nucleic may be determined, according to principles described elsewhere herein.

In addition, in embodiments, compositions and methods described herein for detecting a single nucleotide of interest may also be used to detect multi-nucleotide mutations or polymorphisms.

EXAMPLES

The following examples are offered for illustrative purposes only, and are not intended to limit the present disclosure in any way.

Example 1—Primers for MRSA Detection

Primers were prepared for use in a first amplification reaction for amplifying a first genetic element (mecA) and a second genetic element (orfX from *S. Aureus*) from a common double-stranded nucleic acid molecule. Exemplary genetic element analysis first amplification reaction first primers have the following sequences, in the 5' to 3' direction: GAACCAACGCATGACCCAAG (SEQ ID NO: 3); TTGAACCAACGCATGACCC (SEQ ID NO: 4); CAGAC-GAAAAAGCACCAGAA (SEQ ID NO: 5); GCACCA-GAAAATATGAGCGAC (SEQ ID NO: 6). Exemplary genetic element analysis first amplification reaction second primers have the following sequences, in the 5' to 3' direction: ATCCGGTACTGCAGAACTCA (SEQ ID NO: 7); GCAAATCCGGTACTGCAGAA (SEQ ID NO: 8); ATTG-GCAAATCCGGTACTGC (SEQ ID NO: 9); GGCAGA-CAAATTGGGTGGTT (SEQ ID NO: 10). An exemplary genetic element analysis second amplification reaction first primer has the following sequence, in the 5' to 3' direction: GCCAATGACGAATACAAAGTC (SEQ ID NO: 11). An exemplary genetic element analysis second amplification reaction second primer has the following sequence, in the 5' to 3' direction: TAATAGCCATCATCATGTTTGG (SEQ ID NO: 12).

Example 2—Amplification of Wild-Type and Mutant Hepatitis C NS3 Genes

Figure 3:
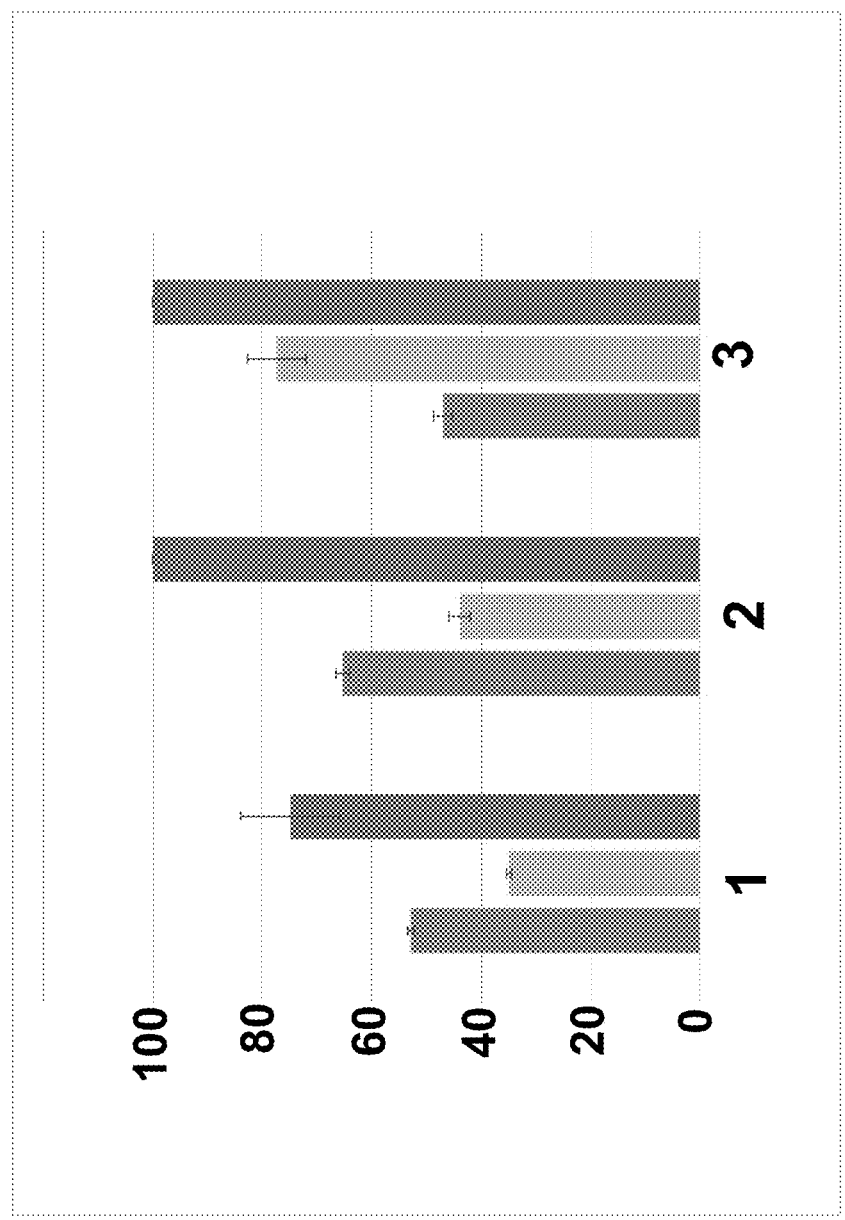
FIG. 3 is a graph depicting results from reactions performed according to a method provided herein.

Nine different reaction mixtures were prepared. Each reaction mixture contained the same reagents and primer concentrations, but the reaction mixtures varied in primers and templates. Of the nine reaction mixtures, three were prepared for each of three different templates: Template 1: wild-type NS3 [nucleotide sequence, in the 5' to 3' direction: GGAACGAGGACCATCGCATCACCCAAGGGTCCT-GTTATCCAGATGTATACCAAT GTAGACCAAGAC-CTCGTGGGCTGGCCCGCTCCTCAAGGTGCCCGCT-CATTGACAC CCTGCACCTGCG (SEQ ID NO: 13)]; Template 2: Q80K mutation NS3 [nucleotide sequence, in the 5' to 3' direction: GGAACGAGGACCATCGCATCAC-CCAAGGGTCCTGTTATCCAGATGTATACCAAT GTA-GACAAAGACCTCGTGGGCTGGCCCGCTCCT-CAAGGTGCCCGCTCATTGACAC CCTGCACCTGCG (SEQ ID NO: 14)]; Template 3: No template control. For each different template, 3 different reaction mixtures were prepared, with each different reaction mixture having a different primer pair: Primer Pair 1: first primer [nucleotide sequence, in the 5' to 3' direction: TTTGTCTAAAGGGTC-CTGTTATCC (SEQ ID NO: 15)], second primer [nucleotide sequence, in the 5' to 3' direction: TAGACAAACAGC-CCACGAGG (SEQ ID NO: 16)]; Primer Pair 2: first primer [nucleotide sequence, in the 5' to 3' direction: TTT-GTCTAGTTATCCAGATGTAT (SEQ ID NO: 17)], second primer [nucleotide sequence, in the 5' to 3' direction: TAGA-CAAACCAGCCCACGAGGTC (SEQ ID NO: 18)]; Primer Pair 3: first primer [nucleotide sequence, in the 5' to 3' direction: TCTTGGTCCAAGGGTCCTGTTATC (SEQ ID NO: 19)], second primer [nucleotide sequence, in the 5' to 3' direction: GACCAAGAAGGGTGTCAATGAGC (SEQ ID NO: 20)]. The reaction mixtures each contained the following reagents: potassium acetate (50 mM); magnesium acetate (10 mM); DTT (1 mM); Tween-20 ® (0.08%); Tris-HCl, pH 7.9 (20 mM); betaine (800 mM); dNTP mixture (1.4 mM each dNTP); Syto Red® (2 uM); Bst DNA polymerase (0.8 U/ul); AMV reverse transcriptase (0.016 U/ul); respective first primer and second primer (0.8 uM each); and respective template. The template sequences were provided in a plasmid. FIG. 3 provides the results of the different amplification reactions. The Y-axis shows the inflection time (in minutes) for the different reactions. The no template reactions show an eventual inflection time due to background signal. On the X-axis, the reactions are grouped together based on the primer pair. From the left to the right, the first group of reactions is with Primer Pair 1, then Primer Pair 2, then Primer Pair 3. Within each group of 3 bars for each Primer Pair, the bars are for the following templates, from left to right: wild-type NS3; Q80K mutation NS3; no template control. As shown in FIG. 3, the wild-type and Q80K mutation templates have different inflection times, depending on the primer pair used to amplify the sequences.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. For example, a feature of one embodiment may be combined with a feature of another embodiment, whether such combination is described herein or not. It should also be understood that while the invention provided herein has been described herein using a limited number of terms and phrases for purposes of expediency, the invention could also be described using other terms and phrases not provided herein which also accurately describe the invention.

It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. The appended claims are not to be interpreted as including means-plus-function limitations, unless such a limitation is explicitly recited in a given claim using the phrase "means for." As used in the description herein and through the claims that follow, a first object described as containing "at least a portion" of a second object may contain the full amount of/the complete second object.

As used in the description herein and throughout the claims that follow, the terms "comprise", "include", and "contain" and related tenses are inclusive and open-ended, and do not exclude additional, unrecited elements or method steps. Also, the presence of broadening words and phrases such as "one or more," "at least," "but not limited to" or other like phrases in some instances shall not be read to mean that the narrower case is intended or required in instances where such broadening phrases may be absent. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction by anyone of the patent documents or the patent disclosure, as they appear in the US Patent and Trademark Office patent file or records, but otherwise reserves all copyright rights whatsoever. The following notice shall apply: Copyright 2014-15 Theranos, Inc.

SEQUENCE LISTING

SEQ ID NO: 1:
GGAACGAGGACCATCGCATCACCCAAGGGTCCTGTTATCCAGATGTATAC
CAATGTAGAC

SEQ ID NO: 2:
CGCAGGTGCAGGGTGTCAATGAGCGGGCACCTTGAGGAGCGGGCCAGCCC
ACGAGGTCT

SEQ ID NO: 3: GAACCAACGCATGACCCAAG

SEQ ID NO: 4: TTGAACCAACGCATGACCC

SEQ ID NO: 5: CAGACGAAAAAGCACCAGAA

SEQ ID NO: 6: GCACCAGAAAATATGAGCGAC

SEQ ID NO: 7: ATCCGGTACTGCAGAACTCA

SEQ ID NO: 8: GCAAATCCGGTACTGCAGAA

SEQ ID NO: 9: ATTGGCAAATCCGGTACTGC

SEQ ID NO: 10: GGCAGACAAATTGGGTGGTT

SEQ ID NO: 11: GCCAATGACGAATACAAAGTC

SEQ ID NO: 12: TAATAGCCATCATCATGTTTGG

SEQ ID NO: 13:
GGAACGAGGACCATCGCATCACCCAAGGGTCCTGTTATCCAGATGTATAC
CAATGTAGACCAAGACCTCGTGGGCTGGCCCGCTCCTCAAGGTGCCCGCT
CATTGACACCCTGCACCTGCG

SEQ ID NO: 14:
GGAACGAGGACCATCGCATCACCCAAGGGTCCTGTTATCCAGATGTATAC
CAATGTAGACAAAGACCTCGTGGGCTGGCCCGCTCCTCAAGGTGCCCGCT
CATTGACACCCTGCACCTGCG

SEQ ID NO: 15: TTTGTCTAAAGGGTCCTGTTATCC

SEQ ID NO: 16: TAGACAAACAGCCCACGAGG

SEQ ID NO: 17: TTTGTCTAGTTATCCAGATGTAT

SEQ ID NO: 18: TAGACAAACCAGCCCACGAGGTC

SEQ ID NO: 19: TCTTGGTCCAAGGGTCCTGTTATC

SEQ ID NO: 20: GACCAAGAAGGGTGTCAATGAGC

We claim:

1. A method for assessing the identity of a nucleotide at a position of interest in a nucleotide sequence in a polynucleotide template, the method comprising:
A) generating multiple copies of a polynucleotide template in a polymerase chain reaction (PCR) amplification reaction mixture, wherein the PCR amplification reaction mixture comprises a PCR amplification reaction first primer and a PCR amplification reaction second primer, wherein in the PCR amplification reaction mixture, the PCR amplification reaction first primer anneals to the polynucleotide template and the PCR second primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template;
B) providing copies of the PCR amplification reaction product generated in step A) in each of at least a non-thermocycling first reaction mixture and a non-thermocycling second reaction mixture, wherein:
the polynucleotide template comprises a first portion, a second portion and a third portion, wherein the third portion is situated in the polynucleotide template between the first portion and the second portion and wherein the position of interest is in the third portion;
the non-thermocycling first reaction mixture comprises copies of the polynucleotide template, a non-thermocycling first primer, and a non-thermocycling second primer, wherein:
the non-thermocycling first primer comprises a first region and a second region, wherein the first region comprises a 5' end of the primer, the second region comprises a 3' end of the primer, and the second region is complementary to the first portion of the polynucleotide template;
the non-thermocycling second primer comprises a first region and a second region, wherein the first region comprises a 5' end of the primer, the second region comprises a 3' end of the primer, and the second region is complementary to a sequence which is complementary to a second portion of the polynucleotide template;
the first region of the non-thermocycling first primer is complementary to the first region of the non-thermocycling second primer; and
the first region of the non-thermocycling second primer is complementary to the third portion of the polynucleotide template;
the second reaction mixture comprises copies of the polynucleotide template, a non-thermocycling third primer, and a non-thermocycling fourth primer, wherein:
the non-thermocycling third primer comprises a first region and a second region, wherein the first region comprises a 5' end of the primer, the second region comprises a 3' end of the primer, and the second region is complementary to the first portion of the polynucleotide template;
the non-thermocycling fourth primer comprises a first region and a second region, wherein the first region comprises a 5' end of the primer, the second region comprises a 3' end of the primer, and the second region is complementary to a sequence which is complementary to a second portion of the polynucleotide template;
the first region of the non-thermocycling third primer is complementary to the first region of the non-thermocycling fourth primer; and
the first region of the non-thermocycling fourth primer is complementary to the third portion of the polynucleotide template; and
the nucleotide sequence of the first region of the non-thermocycling second primer differs from the nucleotide sequence of first region of the non-thermocycling fourth primer by a single nucleotide, wherein the position of the different nucleotide in the non-thermocycling second and non-thermocycling fourth primers corresponds to the position of the nucleotide of interest in the polynucleotide template when the nucleotide sequence of the first region of the non-thermocycling second primer or non-thermocycling fourth primer is oriented with the nucleotide sequence of the third portion of the polynucleotide template for maximum complementation of the sequences;
C) incubating the non-thermocycling first reaction mixture and non-thermocycling second reaction mixture under conditions without thermocycling; and
D) comparing the rate or amount of amplification of the polynucleotide template in the non-thermocycling first reaction mixture to the rate or amount of amplification of the polynucleotide template in the non-thermocycling second reaction mixture, wherein the rate or amount of amplification of the polynucleotide template is indicative of the degree of complementation between first region of the non-thermocycling second or non-thermocycling fourth primer and the nucleotide sequence of the third portion of the polynucleotide template.

2. The method of claim 1, wherein the PCR amplification reaction first primer is at least 10 and no more than 80 nucleotides in length, and wherein when the PCR amplification reaction first primer is annealed to the polynucleotide template, at least 3 nucleotides of the PCR amplification reaction first primer are mis-matched according to Watson-Crick base-pairing rules with corresponding nucleotides on the polynucleotide template.

3. The method 1, wherein the PCR amplification reaction first primer is at least 10 and no more than 80 nucleotides in length, and wherein when the PCR amplification reaction first primer is annealed to the polynucleotide template, at least 5 nucleotides of the PCR amplification reaction first primer are mis-matched according to Watson-Crick base-pairing rules with corresponding nucleotides on the polynucleotide template.

4. The method of claim 1, wherein the PCR amplification reaction second primer is at least 10 and no more than 80 nucleotides in length, and wherein when the PCR amplification reaction second primer is annealed to the polynucleotide which is complementary to the polynucleotide template, at least 3 nucleotides of the PCR amplification reaction first primer are mis-matched according to Watson-Crick base-pairing rules with corresponding nucleotides on the polynucleotide which is complementary to the polynucleotide template.

5. The method claim 1, wherein the PCR amplification reaction second primer is at least 10 and no more than 80 nucleotides in length, and wherein when the PCR amplification reaction second primer is annealed to the polynucleotide which is complementary to the polynucleotide template, at least 5 nucleotides of the PCR amplification reaction first primer are mis-matched according to Watson-Crick base-pairing rules with corresponding nucleotides on the polynucleotide which is complementary to the polynucleotide template.

6. The method claim 1, wherein the position of interest in the nucleotide sequence in the polynucleotide template is a SNP.

7. The method of claim 1, wherein the polynucleotide template is from the hepatitis C virus.

8. The method of claim 7, wherein the polynucleotide template is from the hepatitis C NS3 gene.

9. The method of claim 8, wherein the position of interest in the nucleotide sequence in the polynucleotide template is in the codon encoding $80^{th}$ amino acid of the NS3 gene.

10. The method of claim 1, wherein a concatemer strand comprising at least three copies of the polynucleotide template is generated during the incubation of the non-thermocycling reaction mixture.

* * * * *